US007459155B2

(12) United States Patent
Margolin et al.

(10) Patent No.: US 7,459,155 B2
(45) Date of Patent: Dec. 2, 2008

(54) TREATING ABDOMINAL PAIN DUE TO PANCREATITIS WITH SEAPROSE

(75) Inventors: Alexey L. Margolin, Newton, MA (US); Bhami C. Shenoy, South Grafton, MA (US); Margaret McGrath, Brighton, MA (US)

(73) Assignee: Altus Pharmaceuticals Inc., Cambridge, MA (US)

( * ) Notice: Subject to any disclaimer, the term of this patent is extended or adjusted under 35 U.S.C. 154(b) by 123 days.

(21) Appl. No.: 10/977,737

(22) Filed: Oct. 29, 2004

(65) Prior Publication Data

US 2005/0158299 A1    Jul. 21, 2005

Related U.S. Application Data

(60) Provisional application No. 60/515,552, filed on Oct. 29, 2003, provisional application No. 60/527,490, filed on Dec. 5, 2003.

(51) Int. Cl.
*A61K 38/48* (2006.01)
(52) U.S. Cl. ................................... 424/94.64
(58) Field of Classification Search ........................ None
See application file for complete search history.

(56) References Cited

U.S. PATENT DOCUMENTS

| 4,485,095 | A | 11/1984 | Fujisaki et al. | 424/94 |
| 4,755,383 | A | 7/1988 | Fujii et al. | 424/94 |
| 5,514,373 | A | 5/1996 | Harris, Jr. | 424/94.65 |
| 6,413,512 | B1 | 7/2002 | Houston et al. | 424/94.63 |
| 2001/0006617 | A1 | 7/2001 | Liversidge et al. | 424/1.29 |
| 2003/0026794 | A1 | 2/2003 | Fein | 424/94.2 |
| 2003/0143292 | A1 | 7/2003 | Cho | 424/756 |
| 2004/0038874 | A1 | 2/2004 | Omoigui | 514/12 |
| 2004/0057944 | A1 | 3/2004 | Galle et al. | 424/94 |
| 2004/0092449 | A1 | 5/2004 | Ekwuribe | 514/12 |

FOREIGN PATENT DOCUMENTS

| DE | 3941324 | 11/1990 |
| FR | 2.129.947 | 11/1972 |
| JP | HEI 11-49699 | 2/1999 |
| WO | WO 98/36734 | 8/1998 |

OTHER PUBLICATIONS van Esch et al., Pharmacological management of pain in chronic pancreatitis. Dig Liver Dis. Jul. 2006;38(7):518-26. Epub Apr. 14, 2006. Review.*
Shiratori et al, Clinical evaluation of oral administration of a cholecystokinin-A receptor antagonist (loxiglumide) to patients with acute, painful attacks of chronic pancreatitis: a multicenter dose-response study in Japan. Pancreas. Jul. 2002;25(1):e1-5.*
Ochi et al, Clinical evaluation of cholecystokinin-A- receptor antagonist (loxiglumide) for the treatment of acute pancreatitis. A preliminary clinical trial. Study Group of Loxiglumide in Japan. Digestion. 1999;60 Suppl 1:81-5.*

"American Gastroenterological Association Medical Position Statement: Treatment of Pain in Chronic Pancreatitis," *Gastroenterology*, 115, 763-764 (1998).
Andren-Sandberg, A., "Enzyme Substitution in Pancreatic Disease," *Digestion*, 37(1), 35-46 (1987).
Andren-Sandberg, A., "Theory and Practice in the Individualization of Oral Pancreatic Enzyme Administration for Chronic Pancreatitis," *International Journal of Pancreatology*, 5, 51-62 (1989).
Apte, M.V., et al. "Chronic Pancreatitis: Complications and Management," *J. Clin. Gastroenterol*, 29(3), 225-240 (1999).
Bracale G., et al., "Clinical Study of the Efficacy of and Tolerance to Seaprose S in Inflammatory Venous Disease. Controlled Study Versus Serratio-Peptidase", *Minerva Cardioangiol.*, 44 (10), 515-524 (1996)—English abstract only from PubMed, www.ncbi.nlm.gov.
Braga, P.C., et al., "Effects of Seaprose on the Rheology of Bronchial Mucus in Patients with Chronic Bronchitis. A Double-Blind Study vs. Placebo," *Int. J. Clin. Pharm. Res.*, 13(3), 179-185 (1993).
Braga, P.C., et al., "The Influence of Seaprose on Erythromycin Penetration into Bronchial Mucus in Bronchopulmonary Infections," *Drugs Exptl. Clin. Res.*, 18(3), 105-111 (1992).
Braga, P.C., et al., "In Vitro Rheological Assessment of Mucolytic Activity Induced by Seaprose," *Pharmacological Research*, 22(5), 611-617 (1990).
Brown, A., et al., "Does Pancreatic Enzyme Supplementation Reduce Pain in Patients with Chronic Pancreatitis: A Meta-Analysis," *Am. J. Gastroenterology*, 92(11), 2032-2035 (1997).
Buscher, H.C.J.L., et al., "Bilateral Thoracoscopic Splanchnicectomy in Patients with Chronic Pancreatitis," *Scand J. Gastroenterol.*, Supp. 230, 29-34 (1999).
Copenhagen Pancreatitis Study Group, "Copenhagen Pancreatitis Study, An Interim Report from a Prospective Epidemiological Multicentre Study," *Scand. J. Gastroent.*, 16, 305-312 (1981).
Dindelli, M., et al., "Efficacia clinica e tollerabilita del Seaprose S nel trattamento delle complicanze delle ferite chirurgiche in puerperio", *Minerva Ginecologica*, 42, (7-8), 313-315 (1990)—English abstract only.
DiMagno, E. P., et al., "Impaired Cholecystokinin-Pancreozymin Secretion, Intraluminal Dilution, and Maldigestion of Fat in Sprue," *Gastroenterology*, 63(1), 25-32 (1972).

(Continued)

*Primary Examiner*—Sheridan Swope
(74) *Attorney, Agent, or Firm*—Lowrie, Lando & Anastasi, LLP

(57) ABSTRACT

This invention relates to methods for maintaining the basal level or reducing the level of cholecystokinin (CCK) in blood plasma of a mammal. Additionally, the invention provides methods for treating pain in a mammal and more particularly, methods for treating abdominal pain in a mammal. The methods include administering to the mammal a non-pancreatic protease or a composition comprising a non-pancreatic protease. The methods of this invention are particularly useful for treating abdominal pain in a mammal suffering from acute or chronic pancreatitis and related conditions.

58 Claims, 5 Drawing Sheets

OTHER PUBLICATIONS

Dobrilla, G., "Management of Chronic Pancreatitis," *International Journal of Pancreatology*, 5, 17-29 (1989).

Food and Drug Administration, "75-day Premarket Notification for New Dietary Ingredient," (1998).

Greenberger, N. J., "Enzymatic Therapy in Patients with Chronic Pancreatitis," *Gastroenterology Clinics of North America*, 28(3), 687-692 (1999).

Halgreen, H., et al., "Symptomatic Effect of Pancreatic Enzyme Therapy in Patients with Chronic Pancreatitis," *Scand. J. Gastroent.*, 21, 104-108 (1986).

Isaksson, G., et al., "Pain Reduction by an Oral Pancreatic Enzyme Preparation in Chronic Pancreatitis," *Digestive Diseases and Sciences*, 28 (2), 97-102 (1983).

Lankisch, P.G., "Conservative Treatment of Chronic Pancreatitis," *Digestion*, 37(1), 47-55 (1987).

Layer, P.H., et al., "Klinik und Klassifikation der akuten Pankreatitis," *Praxis*, 392-396—English abstract only.

Lebenthal, E., et al., "Enzyme Therapy for Pancreatic Insufficiency: Present Status and Future Needs," *Pancreas*, 9(1), 1-12 (1994).

Liddle, R. A., et al., "Proteins but not Amino Acids, Carbohydrates, or Fats Stimulate Cholecystokinin Secretion in the Rat," *Am. J. Physiol. Gastrointest. Liver Physiol.*, 251, G243-G248 (1986).

Liddle, R. A., "Regulation of Cholecystokinin Secretion by Intraluminal Releasing Factors," *Am. J. Physiol. Gastrointest. Liver Physiol.*, 269, G319-G327 (1995).

Liddle, R. A., "Regulation of Cholecystokinin Secretion in Humans," *J. Gastroenterology*, 35, 181-187 (2000).

Liddle, R. A., "Cholecystokinin Cells," *Annu. Rev. Physiol.*, 59, 221-242 (1997).

Liddle, R. A., "On the Measurement of Cholecystokinin," *Clinical Chemistry*, 44(5), 903-904 (1998).

Liddle, R. A., "Regulation of Cholecystokinin Synthesis and Secretion in Rat Intestine," *American Institute of Nutrition*, 1308S-1314S (1994).

Luisetti, M., et al., "Some Properties of the Alkaline Proteinase from Aspergillus Melleus," *Int. J. Tiss. Reac.*, 13(4), 187-192 (1991).

Malfertheiner, P., et al., "Effect of Exogenous Pancreatic Enzymes on Gastrointestinal and Pancreatic Hormone Release and Gastrointestinal Motility," *Digestion*, 54(2), 15-20 (1993).

Miyasaka, K., et al., "Feedback Regulation by Trypsin: Evidence for Intraluminal CCK-Releasing Peptide," *Am. J. Physiol. Gastrointest. Liver Physiol.*, 257, G175-G181 (1989).

Moretti, M., et al., "Effects of Seaprose on Sputum Biochemical Components in Chronic Bronchitic Patients: A Double-Blind Study vs Placebo," *Int. J. Clin. Pharm. Res.*, 13(5), 275-280 (1993).

Mossner, J., "Palliation of Pain in Chronic Pancreatitis," *Acute and Chronic Pancreatitis*, 79(4), 861-873 (1999).

Mossner, J., et al., "Treatment of Pain with Pancreatic Extracts in Chronic Pancreatitis: Results of a Prospective Placebo-Controlled Multicenter Trial," *Digestion*, 53, 54-66 (1992).

Mossner, J., "Is There a Place for Pancreatic Enzymes in the Treatment of Pain in Chronic Pancreatitis?" *Digestion*, 54(2), 35-39 (1993).

Niederau, C., et al., "Beneficial Effects of Cholecystokinin-receptor Blockage and Inhibition of Proteolytic Enzyme Activity in Experimental Acute Hemorrhagic Pancreatitis in Mice," *J. Clin. Invest.*, 78, 1056-1063 (1986).

Okhlobystin, A. V., et al., "Enzyme Preparations in Conservative Treatment of Chronic Pancreatitis," TepaneВТИЧeckийapxИВ, No. 10, pp. 86-88 (1998).

O'Sullivan, J. N., et al., "Acute and Chronic Pancreatitis in Rochester, Minnesota, 1940 to 1969," *Gastroenterology*, 62(3), 373-379 (1972).

Otsuki, M., et al., "Bioassay of Plasma Cholecystokinin in Rat and Human: Inhibition of Protein Synthesis Prevents the Decrease in the Sensitivity and Responsiveness of Isolated Rat Pancreatic Acini to CCK-8," *Pancreas*, 4(4), 447-451 (1988).

Patankar, R.V., et al., "Pancreatic Enzyme Supplementation in Acute Pancreatitis," *HPB Surg.*, 8, 159-162 (1995).

Quon, M.G., et al., "Chronic Alcoholic Rats are more Susceptible to Cerulein (CER) Induced Pancreatitis," *Abstracts of the American Pancreatic Association, Pancreas*, 5(6), 727 (1990).

Radun, D., et al., "Chronische Pankreatitis: Konservative Therapie," *Therapeutische Umschau*, 53, 359-364 (1996)—Summary at end of article in English.

Rosewicz, S., et al., "Pancreatic Digestive Enzyme Gene Expression: Effects of CCK and Soybean Trypsin Inhibitor," *Am. J. Physiol. Gastrointest. Liver Physiol.*, 256, G733-G738, (1989).

Rydzewska, Grazyna, et al., "Assessment of the Effectiveness of the Preparation Panzytrat® 20 000 U in the substitutive Treatment of Chronic Pancreatitis," Wiadomości Lekarskie, XLVII, 19-20, pp. 738-744 (1994).

Sidhu, S., et al., "Chronic Pancreatitis: Diagnosis and Treatment," *Postgrad. Med. Journal*, 72, 327-333 (1996).

Simek, M., et al., "Substitution Treatment of Insufficient External Pancreatic Secretion," Vnitřni lék., 39, No. 3, pp. 250-252 (1993).

Schneider, M.U., et al., "Prancreatic Enzyme Replacement Therapy: Comparative Effects of Conventional and Enteric-Coated microspheric pancreatin and acid-stable fungal Enzyme Preparations on Steatorrhoea in Chronic Pancreatitis," *Hepatogastroenterology*, 32(2) 97-102 (1985)—abstract only.

Scolapio, J. S., et al., "Nutrition Supplementation in Patients with Acute and Chronic Pancreatitis," *Pancreas Update*, 28(3), 695-707 (1999).

Sharara, A. I., et al., "Evidence for Indirect Dietary Regulation of Cholecystokinin Release in Rats," *Am. J. Physiol. Gastrointest. Liver Physiol.*, 265, G107-G112, (1993).

Shea, J. C., et al., "An Enteral Therapy Containing Medium-Chain Triglycerides and Hydrolyzed Peptides Reduces Postprandial Pain Associated with Chronic Pancreatitis," *Pancreatology*, 3, 36-40 (2003).

Singh, V. V., "Medical Therapy for Chronic Pancreatitis Pain," *Current Gastroenterology Reports*, 5, 110-116 (2003).

Slaff, J., et al., "Protease-Specific Suppression of Pancreatic Exocrine Secretion," *Gastroenterology*, 87, 44-52 (1984).

Somogyi, L., et al., "Can a meta-Analysis That Mixes Apples With Oranges Be Used to Demonstrate That Pancreatic Enzymes Do Not Decrease Abdominal Pain in Patients With chronic Pancreatitis?" *Am. J. Gastroenterology*, 93, 8, 1396-1398 (1998).

Spannagel, A. W., et al., "Purification and Characterization of a Luminal Cholecystokinin-Releasing Factor from Rat Intestinal Secretion," *Proc. Natl. Acad. Sci.*, 93, 4415-4420 (1996).

Spannagel, A. W., et al. "An Amino-Terminal Fragment of LCRF, LCRF-(1-35), Has the Same Activity as the Natural Peptide," *Am. J. Physiol. Gastrointest. Liver Physiol.*, 273, G754-G758 (1997).

Spannagel, A. W., et al., "Bioactivity of Intraduodenally and Intravenously Infused Fragments of Luminal Cholecystokinin Releasing Factor (LCRF)," *Regulatory Peptides*, 73, 161-164 (1998).

Toskes, P. P., "Medical Management of Chronic Pancreatitis," *Scand. J. Gastroenterol.*, 30(208), 74-80 (1995).

Wang, Y., et al., "Luminal CCK-releasing Factor Stimulates CCK Release from Human Intestinal Endocrine and STC-1 cells," *Am. J. Physiol. Gastrointest. Liver Physiol.*, 282, G16-G22 (2002).

Warshaw, Andrew L., et al., "AGA Technical Review: Treatment of Pain in Chronic Pancreatitis," *Gastroenterology*, 115 765-776 (1998).

Fossati et al., "Antiinflammatory Activity in Rats After Oral Administration of Enteric Coated Microgranules Containing the Proteinase Seaprose-S", Abstract, *European Journal of Pharmaceutical Sciences*, vol. 2, Nos. 1-2:167, 1994.

Kowa Co. Ltd., "Easily Absorbable Enzyme Preparations Comprising Protease and Trypsin Inhibitor and/or Chymotrypsin Inhibitor," Abstract, *WPI/Derwent*, 1981.

Reidelberger, Roger D., "Cholecystokinin and Control of Food Intake", *American Institute of Nutrition*, vol. 124, No. 8:1327S-1333S, 1994.

Weber, et al., "The Effects of Enteric Coated (ECP) Versus uncoated (UCP) Pancreatic Enzyme Supplements on Postprandial Cholecystokinin Levels in Humans: A Prospective, Randomized, Placebo Controlled Trial", Abstract # 207, *Digestive Disease Week Abstracts and Itinerary Planner*, 2003.

Barrett and Rawlings, Perspectives in Biochemistry and Biophysics; Arcives of Biochemistry and Biophysics: 318(2): 247-250 (1995).

Kubota et al., Reversal of Antinociceptive Effect of Cholecystokinin by Benzodiazepines and a Benzodiazepine Antagonist; Japanese Journal of Pharmacology: 37(1): ABSTRACT ONLY (1985).

Rawlings and Barrett, MEROPS: The Peptidase Database; DATABASE MEROPS, Welcome Trust Sanger Institute, Cambridge CB10 1SA, UK; HTTP://MEROPS.SANGER.AC.UK/ (May 26, 2008).

Rose et al., Characterization and Inhibition of a Cholecystokinin-Inactivating Serine Peptidase; Nature: 380 (4):403-309 (1996).

Rosenblum and Kozarich, Prolyl Peptidases: a Serine Proteasse Subfamily with High Potential for Drug Discovery; Curr. Opin. Chem. Biology: 7: 496-504 (2003).

Siezen and Leunissen, Subtilases: The Superfamily of Subtilisin-Like Serine Proteases; Protein Science: 6:501-523 (1997).

Yousef et al., Genomic Overview of Serine Proteases; Biochemical and Biophysical Research Communications: 305: 28-36 (2003).

* cited by examiner

TREATING ABDOMINAL PAIN DUE TO PANCREATITIS WITH SEAPROSE

CROSS-REFERENCE TO RELATED APPLICATIONS

This application claims benefit under 35 U.S.C. § 119(e) of U.S. provisional patent application Nos. 60/515,552, filed Oct. 29, 2003, and 60/527,490, filed Dec. 5, 2003, the disclosures of which are herein incorporated by reference.

TECHNICAL FIELD OF THE INVENTION

This invention relates to methods for maintaining plasma cholecystokinin (CCK) concentration in a mammal. Additionally, the invention provides methods for treating pain in a mammal and more particularly, methods for treating abdominal pain in a mammal. The methods of this invention involve administering to the mammal non-pancreatic proteases or compositions comprising them. These methods are particularly useful for treating abdominal pain in a mammal suffering from acute or chronic pancreatitis.

BACKGROUND OF THE INVENTION

Digestion is the physiological process by which ingested food is broken down into readily absorbed nutrient components, including vitamins and trace elements. Following ingestion, food passes through various segments of the gastrointestinal (GI) tract and digestion is carried out, primarily by digestive enzymes. Three groups of digestive enzymes essential to this process include proteases (for protein digestion), lipases (for fat digestion) and amylases (for carbohydrate digestion).

Food digestion and nutrient absorption occur in the small intestine. There, ingested food is broken down by digestive enzymes for ready absorption. Most digestive enzymes are secreted by the pancreas and arrive in the small intestine through the pancreatic duct.

The observation in the early 1970's that trypsin inhibitors placed into the rat upper small intestine stimulated pancreatic enzyme secretion, led to the understanding that trypsin and chymotrypsin are critical for controlling digestive enzyme secretion by the pancreas (G. M. Green and R. L. Lyman, *Proc. Soc. Exp. Biol. Med.* 140, 6-12 (1972)). Similarly, removal or diversion of bile and pancreatic juice from the upper small intestine was also observed to stimulate pancreatic enzyme secretion. These data suggested the following negative feedback mechanism: the stimulation of pancreatic enzyme secretion is controlled by the level of trypsin activity within the lumen of the small intestine.

In cases of pancreatic insufficiency, the pancreas fails to produce and/or secrete sufficient amounts of digestive enzymes to support normal digestive processes. This failure typically leads to maldigestion, which in turn leads to malabsorption. Pancreatic insufficiency manifests itself in diseases, such as pancreatitis (both acute and chronic forms) and cystic fibrosis, and in some post-operative GI surgeries.

Chronic and acute pancreatitis are diseases characterized by fibrosis and irreversible loss of pancreatic exocrine function. The diseases are also characterized by release and activation of digestive enzymes within the pancreas, leading to autodigestion of the organ itself. While some patients are treated by surgical removal of the parathyroid glands, chronic pancreatitis is largely an untreatable disease worldwide (S. Sidhu and R. K. Tandon, *Postgrad. Med. J.* 72, 327-333 (1996)). The incidence rate for this disease in the United States alone is over 100,000 people each year (Digestive Disease Statistics, NIDDK, 2003).

To date, therapy for pancreatic insufficiency is primarily based on orally-administered porcine pancreatic enzyme extract preparations containing lipase, protease and amylase components. Such enzyme preparations typically include high levels of lipase for treatment of steatorrhea (excretion of fat, due to fat maldigestion/maladsorption); whereas high protease levels are generally thought to be more effective in treating azotorrhea (excretion of protein, due to protein maldigestion/maladsorption). For several reasons, such pancreatic extracts have had limited success for treatment of abdominal pain. Proteases make up only a relatively small proportion of such extracts and within that fraction, a smaller still amount of trypsin.

The mechanism responsible for pain in pancreatic insufficiency patients remains poorly understood (J. Mossner, *Acute and Chronic Pancreatis* 79, 861 (1999); N. J. Greenberger, *Gastroenterol Clin North Am.* 28, 687 (1999)).

One proposed mechanism underlying pain, including abdominal pain, is linked to induction of cholecystokinin (hereinafter "CCK"), a peptide that is released by the mucosal epithelial cells of the duodenum and the enteric nervous system and regulates digestion of nutrients. It has been shown that an increase in CCK stimulates the release of destructive enzymes from the pancreas. The release of CCK from epithelial cells is modulated by the secretion of two other peptides, a monitor peptide and an intestinal CCK releasing factor (CCK-RF), that interact with specific endocrine cell surface receptors (R. A. Liddle, *American Physiological Society*, G319-G327 (1995)). Intraluminal trypsin, which can degrade both of these peptides, inhibits the release of CCK and consequently inhibits pancreatic enzyme secretion. The opposite effect is achieved if trypsin inhibitors and foods are present to serve as trypsin-binding substrates. As a result, a sustained increase in CCK causes a continuous stimulation of pancreatic enzyme production, which in turn may cause pain. Based on this mechanism, one proposed treatment for chronic pancreatitis and its associated pain seeks to control CCK levels using an emulsion containing mixed length polypeptides and a medium chain triglyceride (PCT patent application WO 98/36734).

Although pain reduction has been reported with porcine pancreatic enzyme substitution therapy, the role of proteases generally to treat pain remains unclear. For example, one study demonstrates that intraduodenal perfusion with pancreatic proteases, trypsin and chymotrypsin, but not with amylases or lipases, suppresses pancreatic exocrine secretion in patients suffering from chronic pancreatitis (J. Slaff et al., *Gastroenterology* 87, 44-52 (1984). Other studies report that such pancreatic proteases are not the primary factor in pain reduction but that they instead act synergistically with lipase and amylase components to that end (G. Isaksson and I. Ihse. *Dig. Dis. Sci.* 28, 97-102.(1983); J. Slaff et al. *Gastroenterology* 87, 44-52 (1983)). In contrast, other studies report no amelioration of pain following pancreatic protease or extract treatments (H. Halgreen et al. *Scand. J. Gastroenterol.* 21, 104-108 (1986); J. Mössner et al., *Digestion* 53, 54-66 (1992)). In some instances, patients treated with large amounts of enzymes have been prone to develop abdominal cramps (P. G. Lankisch, *Digestion* 37, 47-55 (1987)).

Despite efforts to delineate the role of pancreatic proteases for treatment of pain, including abdominal pain in pancreatitis, the need still exists for further therapy regimens. The present invention addresses that need.

SUMMARY OF THE INVENTION

The present invention is directed to methods for maintaining a basal level of plasma cholecystokinin (CCK) concentration or reducing plasma CCK concentration in a mammal. The invention further provides methods for treating pain, specifically abdominal pain, in a mammal by administering to said mammal a non-pancreatic protease or compositions thereof. According to this invention, the crystalline, semi-crystalline or amorphous form of a non-pancreatic protease, or compositions thereof, may be advantageously used in methods for treating a mammal suffering from pain in chronic or acute pancreatitis or related conditions. In a preferred embodiment of this invention, the non-pancreatic protease is in the form of protease crystals.

Other objects of the invention will be appreciated by those skilled in the art, in view of the disclosure herein.

DETAILED DESCRIPTION OF THE INVENTION

Figure 1:
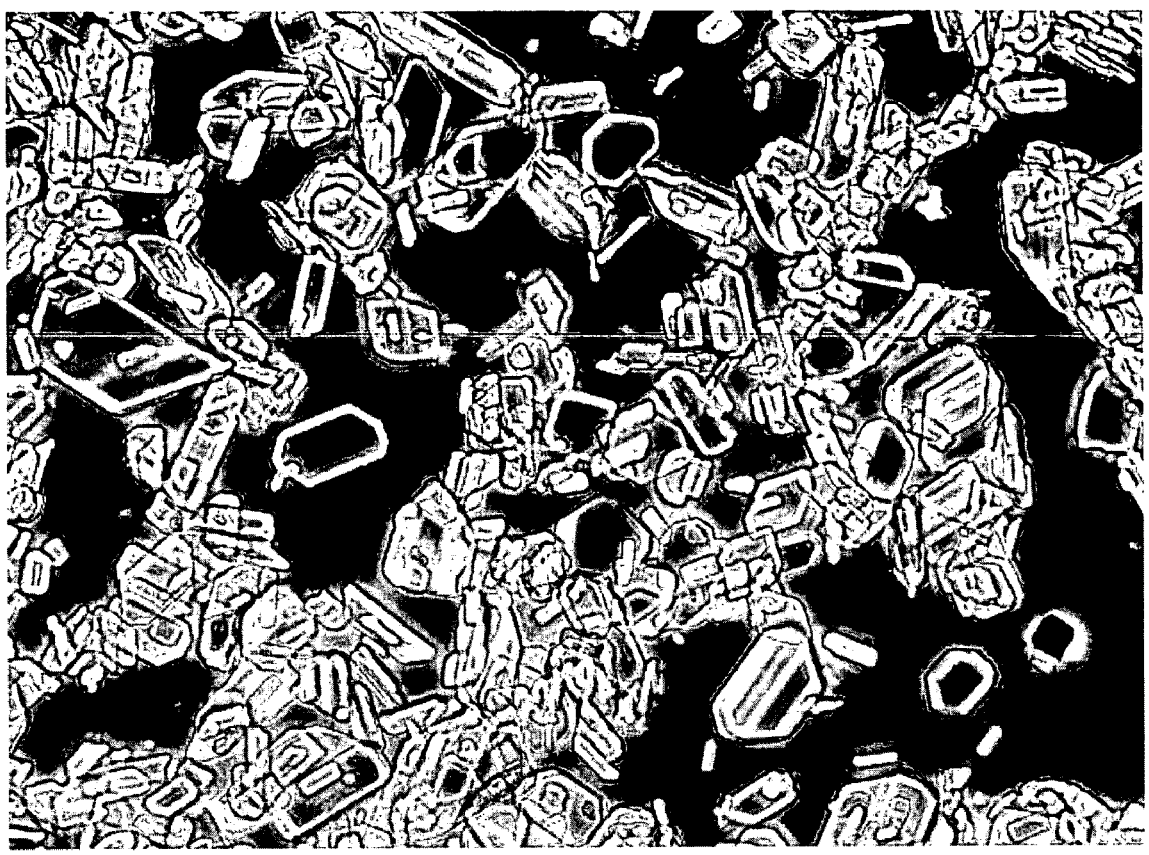
FIG. 1 illustrates seaprose crystals grown in the presence of 10 mM sodium carbonate (pH 9.5), as imaged by optical microscopy. See Example 1.

The present invention relates to the discovery that non-pancreatic proteases can be used to maintain a basal level of CCK concentration or reduce CCK concentration in mammalian plasma. Non-pancreatic proteases in all forms, including crystalline, semi-crystalline, liquid and amorphous forms, are particularly useful for controlling CCK concentration in plasma, in turn leading to a reduction in pain. Specific proteases, such as seaprose, serrapeptase (or serratiopeptidase), pronase or a pronase component, or mixtures thereof, are particularly advantageous for this purpose.

Definitions

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

The following terms, unless otherwise indicated, shall be understood to have the following meanings:

The term "cholecystokinin" ("CCK") refers to an integrative, regulatory peptide that is released from secretory cells and nerve fibers in the mammalian upper intestine. This peptide or hormone is secreted into the blood upon the ingestion of proteins and fats. The physiologic actions of CCK include, but are not limited to, stimulation of pancreatic secretion and gallbladder contraction, regulation of gastric emptying, and induction of satiety. CCK thus serves to regulate, in a highly coordinated manner, the digestion of nutrients. The brain produces and processes mainly the COOH-terminal linear octapeptide of CCK (CCK-8), while the gut produces larger forms of the peptide, such as CCK-58, -33, and -22. While CCK in tissue and blood ranges from 4-83 amino acids in size, smaller forms (such as CCK-8) display the biological activity of larger forms in both the brain (as a neurotransmitter) and the peripheral system (as a hormone). CCK is found predominantly as a neuropeptide that plays modulatory roles in a variety of behavioral states and disorders.

The term "feeding peptide" refers generally to a class of integrative peptides that influence the regulation of feeding and food intake through the peripheral system, as well as the central nervous system ("CNS"). As used herein, feeding peptides can be distinguished from the more general class of regulatory peptides that have more limited or less well-documented integrative functions in the periphery. CCK has also been referred to in the art as a feeding peptide.

The term "food" encompasses any substance that can be ingested by a mammal or delivered to a mammal by non-oral means, to yield energy. As used herein, food includes any sustenance in any form, including for example, solid or liquid form, and including for example, nutritional supplements.

The term "monitor peptide", also referred to as pancreatic secretory trypsin inhibitor ("PSTI"), stimulates the growth of intestinal epithelial cells and induces secretion of pancreatic enzymes into the mammalian small intestine. Monitor peptide is commonly activated in response to protein intake and induces the secretion and release of CCK from the intestine. It is also commonly referred to in the art as "trypsin-sensitive CCK-releasing peptide" (S. Tsuzuki et al., *Eur. J. Biochem.* 199, 245-252 (1991); R. Yamanishi et al., *Biochem. J.* 291, 57-63 (1993)).

The term "intestinal CCK-releasing factor" refers to a factor of intestinal origin that has been partially characterized and is thought to play a role in the stimulation of CCK secretion following the ingestion of protein or fats. Through mechanisms largely unknown, this and other CCK releasing factors (namely monitor peptides) are thought to provide positive and negative-feedback mechanisms for the regulation of CCK secretion.

The term "mammal" refers to a human or animal. For example, an animal may be a non-human primate, rodent, canine, pig, cat, cow, horse and goat. In a preferred embodiment of this invention, the mammal is human.

The term "maldigestion" refers to the impaired breakdown of nutrients (such as carbohydrates, proteins, fats) into their absorbable constituents (mono-, di-, or oligosaccharides, amino acids, oligopeptides, fatty acids and monoglycerides).

The term "malabsorption" refers to the impaired absorption of digested nutrients, including vitamins and trace elements, from the small intestine or large bowel. It may be due to defective mucosal uptake by the intestinal lining or particular abnormalities of digestion. Intestinal malabsorption may occur for many nutrients or for specific macronutrients, namely carbohydrates, fats or proteins, as well as for micronutrients, such as calcium, magnesium, iron, and vitamins. Malabsorption may result from several conditions, some of which include, for example, lactose intolerance, celiac disease, Crohn's disease and pancreatic insufficiency, bacterial overgrowth, short bowel syndrome, amyloidosis, short bowel diverticulae, scleroderma, tropical sprue, helicobacter pylori infection, radiation therapy, chemotherapy, thoracic duct obstruction, such as intestinal lymphangiectasia, eosinophilic enteritis, lymphoma, mastocytosis, protein-losing enteropathy and menetrier's disease.

The term "chronic pancreatitis" refers to a recurring process in which autodigestion of pancreatic tissue occurs by its own enzymes. In this disease, pancreatic enzymes that normally facilitate nutrient digestion become activated within and escape or leak from the pancreatic duct or acinar cells into the pancreas where they induce tissue necrosis. Chronically, such action can lead to long-term morphological and functional loss of the organ. The two most frequent types of chronic pancreatitis in adults are alcohol-induced and idiopathic pancreatitis. In children, chronic pancreatitis is frequently caused by cystic fibrosis.

"Acute pancreatitis" is an acute inflammatory process of the pancreas that can involve peripancreatic tissues or remote organ systems, or both. It may occur as an isolated attack or recur in distinct episodes with reversion to normal histology between attacks. By definition, acute pancreatitis is reversible; it is distinguished from chronic pancreatitis by the absence of continuing inflammation, irreversible structural changes, and permanent impairment of exocrine and endocrine pancreatic function. Acute pancreatitis is classified further into mild and severe forms. Mild acute pancreatitis is associated with minimal organ dysfunction and uneventful recovery. Severe acute pancreatitis is associated with pancreatic necrosis and may lead to organ failure and/or local complications. Local complications of acute pancreatitis include fluid collections, pseudocyst formation, abscess, pancreatic necrosis, hemorrhage, venous thrombosis, and pseudoaneurysm formation.

The term "pain" refers to a sensory experience associated with actual or potential tissue damage. The physical sensation of pain may arise from a discrete cause and constitute an associated symptom of a disease, or the pain itself may be a syndrome which constitutes the primary problem, e.g. neuropathic pain. In one embodiment of this invention, pain is not caused or accompanied by any autoimmune or inflammatory response or disease. In another embodiment of this invention, the term "abdominal" pain does not include female pelvic pain due to gynecological functions or diseases. In another embodiment of this invention, the term "abdominal" pain does not include female chronic pelvic pain syndrome, including chronic parametritis.

The term "protease" refers to a proteinase, proteolytic enzyme or peptidase, which is any enzyme that catalyzes the splitting of interior amide peptide bonds in a protein. Specifically, proteases catalyze the conversion of proteins into their component amino acids by cleaving the amide linkage between the carboxyl group of one amino acid and the amino group of another. Proteases are generally identified by their catalytic type, e.g., aspartic acid peptidases, cysteine (thiol) peptidases, metallopeptidases, seine peptidases, threonine peptidases, alkaline or semi-alkaline protease, neutral, and peptidases of unknown catalytic mechanism (see the MEROPS peptidase database). According to a preferred embodiment, the proteases useful in the methods of this invention are non-pancreatic proteases. The term "non-pancreatic proteases" refers to proteases which are: (1) not purified from human or animal pancreas tissue or extracts and (2) do not include trypsin and optionally (3) do not include chymotrypsin, whether or not the trypsin or chymotrypsin is purified from human or animal pancreas tissue or extracts or produced in a microbial or unicellular host. According to a preferred embodiment of this invention, non-pancreatic proteases are produced in a microbial or unicellular host. Such unicellular hosts may be selected from any one of bacteria, yeast, fungi, plant, insect or mammalian cells in culture. According to a preferred embodiment of this invention, the non-pancreatic protease is produced by Aspergillus melleus. Alternatively, the non-pancreatic proteases useful in this invention may be synthesized by conventional peptide synthesis techniques.

"Seaprose" ("SAP") refers to a homogeneous crystalline semi-alkaline proteolytic enzyme produced by *Aspergillus melleus* and is commercially-available from Amano Enzyme Inc., Japan. SAP may be prepared by either a liquid or solid fermentation process. Seaprose has also been referred to as seaprose-S, *Aspergillus* alkaline proteinase; aspergillopeptidase B; API 21; aspergillopepsin B; aspergillopepsin F; *Aspergillus candidus* alkaline proteinase; *Aspergillus flavus* alkaline proteinase; *Aspergillus melleus* semi-alkaline proteinase; *Aspergillus oryzae* alkaline proteinase; *Aspergillus parasiticus* alkaline proteinase; *Aspergillus serine* proteinase; *Aspergillus sydowi* alkaline proteinase; *Aspergillus soya* alkaline proteinase; *Aspergillus melleus* alkaline proteinase; *Aspergillus sulphureus* alkaline proteinase; prozyme; P 5380; kyorinase; semi-alkaline protease; sumizyme MP; prozyme 10; onoprose; onoprose SA; protease P; promelase, alkaline proteinase (*Penicillin citrinum*); alkaline proteinase (*Aspergillus* sp.); allergen Asp fl 1 (*Aspergillus flavus*); allergen Asp fl 13 (*Aspergillus flavus*); allergen Asp f 13 (*Aspergillus fumigatus*); allergen Pen c2 (*Penicillium citrinum*); aspergillopeptidase B; PepD; prtA and SUB2 (*Microsporum canis*). Seaprose has a molecular weight of approximately 30 kD and is stable within a range of pH 5.0-9.0. In addition, seaprose is a protease involved in enzymatic cleavage and more specifically, it cleaves preferentially the substrate containing a Phe residue in the $P_1$ position of the protein chain. According to one embodiment of this invention, one or more forms or types of seaprose may be used. Alternatively, seaprose may be used in combination with one or more non-pancreatic proteases other than seaprose.

The term "lipase" refers to an enzyme that catalyzes the hydrolysis, i.e., separating the hydroxyl group and the hydrogen atom of compounds into fragments by the addition of water, of lipids to glycerol and simple fatty acids. This enzymatic reaction usually requires calcium ions ($Ca^{2+}$). Lipases secreted by the pancreas are highly important for the digestion of fat (triglycerides) in the upper loop of the small intestine. Lipases, e.g., may be derived from animal sources or prepared from microbial or unicellular sources.

The term "amylase" refers to an enzyme that is produced in the pancreas and also the salivary glands in humans but not all mammals. Human salivary amylase is known as ptyalin. Amylase is the main digestive enzyme responsible for digesting carbohydrates, e.g., polysaccharides, by catalyzing the conversion of the two components of starch (amylose and amylo-pectin) into simple sugars in the small intestine. More specifically, amylase hydrolyzes starch, glycogen, and dextrin to form glucose, maltose, and the limit-dextrins. Clinically, blood amylase levels are often elevated in conditions of acute and sometimes chronic pancreatitis. Amylases, e.g., may be derived from animal sources or prepared from microbial or unicellular sources.

While the terms "protease", "amylase" and "lipase" are more or less universally known in the art as the three primary classes of digestive enzymes, there are many types of enzymes that fit with each of these classes and perform distinctly specialized functions. For example, proteolytic enzymes that assist in pancreatic function include endopeptidases (trypsin, chymotrypsin, elastase and kallikrein) and exopeptidases (carboxypeptidase A and carboxypeptidase B) (E. Lebenthal et al., *Pancreas* 9, 1-12(1994)). Other examples of proteases include bacillolysin, bromelain, ficin, oryzin, papain, pepsin, pronase, Proteinase K, Proteinase S, seaprose, serrapeptidase, subtilisin, thermolysin, thrombin, and other similar enzymes. A summary of non-pancreatic proteases that can be used in connection with this invention are exemplified below in Table 1.

TABLE 1

| Protease | Species |
| --- | --- |
| metalloprotease | *Serratia marcescens* |
| Serratia Protease (E.C.3.4.24.40) (Serralysin) | *Serratia* sp. (strain E-15) |
| metalloprotease p1 | *Yersinia ruckeri* |
| metalloproteinase (EC 3.4.24.—) | *Erwinia chrysanthemi* |
| protease A | *Erwinia chrysanthemi* |
| metalloprotease | *Pectobacterium carotovorum* subsp. *carotovorum*. |
| organic solvent-tolerant protease | *Pseudomonas aeruginosa* |
| alkaline metalloproteinase | *Pseudomonas aeruginosa* PAO1 |
| metalloprotease | *Pseudomonas fluorescens* |
| serralysin | *Pseudomonas* sp. 'TAC II 18' |
| alkaline protease | *Pseudomonas fluorescens* |
| APrA | *Pseudomonas brassicacearum* |
| alkaline metalloproteinase | *Photorhabdus luminescens* |
| metalloprotease | *Proteus mirabilis* |
| metalloprotease | *Yersinia pseudotuberculosis* IP 32953 |
| metalloprotease | *Yersinia pestis* CO92 |
| alkaline metalloproteinase | *Caulobacter crescentus* CB15 |
| RB140 | *Ruegeria* sp. PR1b |
| protease-like protein | *Azospirillum brasilense* |
| b116027 | *Bradyrhizobium japonicum* USDA 110 |
| protease | *Sinorhizobium meliloti* 1021 |
| rhizobiocin RzcA | *Rhizobium leguminosarum* bv. *Trifolii* |
| Protease | *Azotobacter vinelandii* |
| Protease | *Pseudomonas putida* KT2440 |
| matrilysin | *Mus musculus* |
| Protease | *Nostoc* sp. PCC 7120 |
| alkaline protease | *Aspergillus fumigatus* |
| alkaline protease | *Aspergillus* sp. MK245 |
| alkaline protease | *Aspergillus* sp. MK285 |
| oryzin (EC 3.4.21.63) | *Aspergillus oryzae* |
| alkaline protease | *Aspergillus viridinutans* |
| allergen Asp fl 1 | *Aspergillus flavus* |
| protease | *Aspergillus niger* |
| alkaline proteinase | *Trichoderma hamatum* |
| extracellular serine protease; Tvsp1 | *Hypocrea virens* |
| alkaline proteinase (EC 3.4.21.—) | *Acremonium chrysogenum* |

TABLE 1-continued

| Protease | Species |
| --- | --- |
| Protease | *Gibberella zeae* PH-1 |
| subtilase | *Ophiostoma piceae* |
| subtilisin-like protease | *Verticillium dahliae* |
| subtilisin-like proteinase Mp1 | *Magnaporthe poae* |
| Protease | *Magnaporthe grisea* 70-15 |
| subtilisin-like serine protease PR1A | *Metarhizium anisopliae* var. *anisopliae* |
| serine protease | *Tolypocladium inflatum* |
| subtilisin-like protease PR1D | *Metarhizium anisopliae* var. *acridum* |
| subtilisin-like protease SUB2 | *Arthroderma benhamiae* |
| serine protease | *Paecilomyces lilacinus* |
| Protease | *Neurospora crassa* |
| subtilisin-like protease | *Phaeosphaeria nodorum* |
| subtilisin-like protease 2 | *Microsporum canis* |
| subtilisin-like protease SUB2 | *Trichophyton rubrum* |
| Protease | *Leptosphaeria maculans* |
| alkaline serine protease ver112 | *Lecanicillium psalliotae* |
| alkaline serine protease | *Verticillium chlamydosporium* var. *chlamydosporium* |
| cuticle-degrading protease | *Cordyceps brongniartii* |
| Protease | *Neurospora crassa* |
| alkaline serine protease | *Penicillium chrysogenum* |
| serine proteinase | *Agaricus bisporus* |
| subtilase-type proteinase isp6 | *Schizosaccharomyces pombe* |
| cuticle-degrading protease bassiasin I | *Beauveria bassiana* |
| subtilase | *Ophiostoma piliferum* |
| vacuolar serine protease | *Penicillium oxalicum* |
| Pen c 1; alkaline serine protease | *Penicillium citrinum* |
| subtilisin-like protease SUB3 | *Trichophyton rubrum* |

The proteases, as well as any other enzymes useful in the methods of this invention, may be derived from microbial, bacterial, fungal, plant or animal origin, including those produced by recombinant DNA technology. Alternatively, they may be produced by conventional peptide synthesis techniques. According to a preferred embodiment, the proteases useful in the methods of this invention are non-pancreatic proteases. In preferred embodiments of this invention, the non-pancreatic protease is seaprose, serrapeptase, pronase, a pronase component, or a mixture thereof. Examples of pronases include: Proteinase A, Proteinase B, metalloendopeptidase and metalloproteinase. Characteristics of preferred non-pancreatic proteases and their uses to date are enumerated below in Table 1a.

TABLE 1a

| | Seaprose (SAP) | Serrapeptase | Pronase |
| --- | --- | --- | --- |
| Protein Seq. | 282 amino acids | 470 amino acids | Pronase is a mixture of endo- and exo-proteinases. It cleaves almost any peptide bond Proteinase A-297 amino acid Proteinase B-299 amino acid Neutral Metalloproteinase-Mycolysin Metalloendopeptidase - 334 amino acids |
| Mol. Wt | 28.5 kD | 50.5 kD | Proteinase A - 29.7 kD |
| PI | 5.84 | 4.61 | Proteinase A - 9.04 |
| Stability | PH 5 to 9.0 | Metalloprotein Zn Inactivated by acidic pH | Pronase requires calcium ions. It retains activity in 1% SDS and 1% Triton X. |

TABLE 1a-continued

|  | Seaprose (SAP) | Serrapeptase | Pronase |
|---|---|---|---|
| Crystal Structure | available | available | Some components of the mixture are very stable to urea and guandinium HCl, but complete digestion will not occur Proteinase A, Proteinase B and Metalloendopeptidase are available |
| Host | Aspergillus melleus | Serratia marcescens | Streptomyces griseus |
| Substrate specificity | Non-specific | Non-specific | Non-specific |
| Optimum pH | pH 8 | pH 9-10 | pH 7.5; 7-8. Different components of the mixture may have different optima |
| Indications | Anti-inflammatory action Expectorant | anti-inflammatory agent Heart disease anti-bacterial infection hastens wound healing engorgement of breast cystitis, epididymitis, pericoronitis Inadequate expectoration of sputum in bronchitis | Relief of swelling, difficulty in expectoration |
| Manufacturers/ distributors | Amano Enzyme Inc., Japan (SAP used herein was prepared by solid fermentation process) | GHARPURE LABORATORIES PVT. LTD. Takeda Chemical Industries, Ltd. | EMD Chemicals Inc. Kaken Pharmaceutical Co., Japan |

The dosage form of a non-pancreatic protease or composition comprising a non-pancreatic protease for use in the methods of this invention may be that of a liquid, solid, suspension or dispersion. The dosage route for a non-pancreatic protease or composition comprising a non-pancreatic protease may be by any conventional administration route, including, for example, oral route, enteral route, transdermal route or parenteral route. Finally, a non-pancreatic protease or composition comprising a non-pancreatic protease may be administered as a slurry, tablet, scored tablet, coated tablet, caplet, capsule or dragee.

As used herein, a therapeutically effective amount of a non-pancreatic protease is from about 5,000 to about 1,000,000 United States Pharmacopeia (USP) units of protease activity per dose. In a preferred embodiment, the therapeutically effective amount of a non-pancreatic protease is from about 5,000 to 750,000 USP units of protease activity per dose. In yet another preferred embodiment, the therapeutically effective amount of a non-pancreatic protease is from about 5,000 to 500,000 USP units of protease activity per dose. In a more preferred embodiment, the therapeutically effective amount of a non-pancreatic protease is from about 5,000 to 250,000 USP units of protease activity per dose. For all of these activity unit ranges, one USP unit of protease is defined in the "Assay of Protease Activity" (U.S. Pharmacopeia/National Formulary, USP 26/NF21, 2003 pg 1389-1391). Where the methods of treatment are carried out using a therapeutically effective amount of a composition comprising a non-pancreatic protease, such an amount is one which provides one of the aforementioned activity units of protease per dose of formulation.

Alternatively, according to this invention, a non-pancreatic protease or composition comprising a non-pancreatic protease is administered to a mammal in a form that has an active protease level of between about 20 mg to about 500 mg per meal. In another embodiment, a non-pancreatic protease or composition comprising a non-pancreatic protease is administered to a mammal in a form that has an active protease level of between about 50 mg to about 500 mg per meal. In an alternate embodiment, a non-pancreatic protease or composition comprising a non-pancreatic protease is administered to a mammal in a form that has an active protease level of between about 50 mg to about 250 mg per meal. Activity is measured as defined above.

In an alternative embodiment, a non-pancreatic protease or composition comprising a non-pancreatic protease is administered to a mammal such that the overall active protease dose per meal is between about 1 mg per kg mammal body weight and about 10 mg per kg mammal body weight, preferably between about 1 mg per kg mammal body weight and about 3 mg per kg mammal body weight or preferably between about 1 mg per kg mammal body weight and about 2 mg per kg mammal body weight.

Non-pancreatic proteases according to this invention may be crystalline, semi-crystalline or amorphous in form. As used herein, the term "amorphous" includes amorphous solids, as well as liquids. Non-pancreatic proteases may be crystallized to form perfectly crystalline materials in the solid state or may be present as amorphous (completely non-crystalline) or semi-crystalline (having crystalline and amorphous regions) forms in the solid state. For example, crystals display characteristic features including a lattice structure, characteristic shapes and optical properties, such as refractive index. A crystal consists of atoms arranged in a pattern that repeats periodically in three dimensions. On the other hand, an amorphous solid has no molecular lattice structure characteristic of the crystalline solid state. Non-pancreatic protease crystals may be in crosslinked or non-crosslinked form. In addition, amorphous forms of such non-pancreatic proteases can also be in crosslinked or non-crosslinked form.

The term "basal level" or "basal concentration" refers to the level or concentration of CCK in plasma in a particular patient or mammal after overnight fasting. Once food is ingested, the CCK concentration in plasma increases above basal level, which in turn, stimulates the pancreas to secrete pancreatic juice that includes enzymes and bicarbonate.

As used herein, the phrase "maximum plasma concentration ($C_{max}$)" refers to peak plasma concentration measured after administration of food. The value for $C_{max}$ is obtained by subtracting the basal concentration from the peak plasma concentration.

When used according to one embodiment of this invention, the term "reducing" or "reduction" refers to a percent reduction in a mammal's $C_{max}$ after the administration of food. This reduction is measured by comparing (a) $C_{max}$ in a mammal after food administration in the absence of a non-pancreatic protease to (b) $C_{max}$ after food administration in the presence of the non-pancreatic protease. If the percent reduction in $C_{max}$ is 100%, then the non-pancreatic protease "maintains" a CCK concentration at the basal concentration. If the percent reduction in greater than 100%, then the non-pancreatic protease reduces the CCK concentration below the basal level. According to another embodiment of this invention, "reducing" or "reduction" refers to the reduction of CCK concentration relative to the basal concentration in the absence of food administration in a particular mammal. For example, a non-pancreatic protease that is administered in the absence of food may reduce the CCK concentration below the basal concentration. This may be desired, for example, in the treatment of gastrointestinal disease, malabsorption syndromes, acute and chronic infections and eating disorders, such as anorexia nervosa. In yet a further embodiment of this invention, the term "reducing" or "reduction" refers to any reduction in the CCK concentration in a particular mammal measured at any time without fasting prior to administration of a non-pancreatic protease.

Non-pancreatic proteases useful in the methods of this invention may be combined with an excipient. According to this invention, an "excipient" acts as a filler or a combination of fillers used in pharmaceutical compositions. Preferred excipients included in this category are: Salts of either 1) amino acids such as glycine, arginine, aspartic acid, glutamic acid, lysine, asparagine, glutamine, proline; 2) carbohydrates, e.g., monosaccharides such as glucose, fructose, galactose, mannose, arabinose, xylose, ribose; 3) disaccharides, such as lactose, trehalose, maltose, sucrose; 4) polysaccharides, such as maltodextrins, dextrans, starch, glycogen; 5) alditols, such as mannitol, xylitol, lactitol, sorbitol; 6) glucuronic acid, galacturonic acid; 7) cyclodextrins, such as methyl cyclodextrin, hydroxypropyl-β-cyclodextrin and alike; 8) inorganic molecules, such as sodium chloride, potassium chloride, magnesium chloride, phosphates of sodium and potassium, boric acid, ammonium carbonate and ammonium phosphate; 9) organic molecules, such as acetates, citrate, ascorbate, lactate; 10) emulsifying or solubilizing/stabilizing agents like acacia, diethanolamine, glyceryl monostearate, lecithin, monoethanolamine, oleic acid, oleyl alcohol, poloxamer, polysorbates, sodium lauryl sulfate, stearic acid, sorbitan monolaurate, sorbitan monostearate, and other sorbitan derivatives, polyoxyl derivatives, wax, polyoxyethylene derivatives; and 11) viscosity increasing reagents like, agar, alginic acid and its salts, guar gum, pectin, polyvinyl alcohol, polyethylene oxide, cellulose and its derivatives propylene carbonate, polyethylene glycol, hexylene glycol, tyloxapol. A further preferred group of excipients includes sucrose, trehalose, lactose, sorbitol, lactitol, inositol, salts of sodium and potassium such as acetate, phosphates, citrates, borate, glycine, arginine, polyethylene oxide, polyvinyl alcohol, polyethylene glycol, hexylene glycol, methoxy polyethylene glycol, gelatin, hydroxypropyl-β-cyclodextrin, polylysine, polyarginine.

In one embodiment of this invention, the excipient is selected from the group consisting of: salts, alcohols, carbohydrates, proteins, lipids, surfactants, polymers and polyamino acids. In another embodiment, the excipient is selected from the group consisting of: Protamine, polyvinylalcohol, cyclodextrins, dextrans, polyamino acids, such as polyarginine, polylysine and poly glutamate, polyethylene glycol and dendrimers, polymers such as polycarbophil and alginate.

According to this invention, non-pancreatic proteases may also be combined with one or more other therapeutic agents. Examples of therapeutic agents include, for example, enzymes, such as amylase and/or lipase, preferably produced in a unicellular or microbial host or by conventional peptide synthesis techniques.

According to the present invention, non-pancreatic proteases, whether in crystal or non-crystal form, may be crosslinked in order to impart stability to their structure. Useful crosslinkers include, but are not limited to, the following multifunctional crosslinkers, as shown in Table 2. Procedures for crosslinking may be performed according to any conventional crosslinking technique.

TABLE 2

Crosslinkers

| Crosslinker Class | Crosslinker |
|---|---|
| Homobifunctional | dithiobis(succinimidylpropionate) (DSP); 3,3'-dithiobis(sulfosuccinimidyl-proprionate) (DTSSP); dimethyl 3,3'-dithiobispropionimidate.HCl (DTBP); bismaleimidohexane (BMH); bis[sulfosuccinimidyl] suberate (BS); 1,5-difluoro-2,4-dinitrobenzene (DFDNB); dimethyl-suberimidate.2HCl (DMS); disuccinimidyl glutarate (DSG); disulfosuccinimidyl tartarate (Sulfo-DST); ethylene glycolbis [sulfosuccinimidylsuccinate] (Sulfo-EGS); Bis-(β-[4-azidosalicylamido]ethyl) disulfide (BASED); 1,4-di-(3'-[2'-pyridyldithio]propionamido) butane (DPDPB) and (Bis[2-(sulfosuccinimidooxycarbonyloxy) ethyl] sulfone (Sulfo-BSOCOES) |
| Heterobifunctional | N-succinimidyl-3-(2-pyridyldithio) propionate (SPDP); succinimidyl-6-(3-[2-pyridyldithio] propionate)hexanoate (LC-SPDP); sulfosuccinimidyl-6-(3-[2-pyridyldlthio] propionate) hexanoate (Sulfo-LC-SPDP); N-(4-[p-azidosalicylamido]butyl)-3'-(2'-pyridyldithio) propionamide (APDP); N-succinimidyl(4-azidophenyl)1,3'-dithiopropionate (SADP); sulfosuccinimidyl(4-azidophenyl) 1,3'-dithiopropionate (Sulfo-SADP); sulfosuccinimidyl-2-(7-azido-4-methycoumarin-3-acetamide)ethyl-1,3'dithiopropionate (SAED); sulfosuccinimidyl-2-(m-azido-o-nitrobenzamido)ethyl-1,3'-dithiopropionate (SAND); sulfosuccinimidyl-2-(p-azidosalicylamido)ethyl-1,3'-dithiopropionate (SASD); succinimidyl-4-(p-maleimidophenyl)butyrate (SMPB); sulfosuccinimidyl-4-(p-maleimidophenyl)butyrate (Sulfo-SMPB); 4-succinimidyloxycarbonyl-methyl-α-(2-pyridylthio) toluene (SMPT); sulfosuccinimidyl-6-(α-methyl-α-(2-pyridylthio) toluamido)hexanoate (Sulfo-LC-SMPT); N-hydroxysulfo-succinimidyl-4-azidobenzoate (Sulfo-HSAB); N-[γ-maleimido-butyryloxy] succinimide ester (GMBS); and NHS-PEG-Vinylsulfone (NHS-PEG-VS) |
| Zero-order | 1-ethyl-3-[3-dimethylaminopropyl]carbodiimide hydrochloride (EDC); and Sufo-NHS |
| Dialdehydes | glutaraldehyde, succinaldehyde, octanedialdehyde and glyoxal |
| Other | halo-triazines, halopyrimidines, anhydrides of aliphatic or aromatic mono- or dicarboxylic acids, halides of aliphatic or aromatic mono-or dicarboxylic acids, N-methylol compounds, diisocyanates, diisothiocyanates and aziridines |

Methods for Maintaining Basal CCK Levels or Reducing CCK Levels in Mammalian Blood Plasma Because CCK is an abundant and widely distributed mammalian peptide, many diseases or disturbances may be advantageously treated by maintaining the level of CCK using a non-pancreatic protease or composition thereof according to this invention. Disease states that are or may be mediated by CCK include, but are not limited to, pancreatitis (acute or chronic), protein malabsorption (azotorrhea), lipid malabsorption (steatorrhea), gastro-intestinal disturbances, gall bladder disease, cerebrovascular accident ("CVA"), gastroesophageal disease, peptic ulcer disease, gastrinomas, intestinal motility disorders, sphincter of oddi dysfunction, cholelithiasis, choledocholithiasis, biliary colic, ascending cholangitis, eating disorders, obesity, drug addiction (CCK is highly present in striatum and co-distribution of CCK and dopamine systems links endogenous CCK with reward, psychostimulant sensitization and habit-forming properties of drugs in motivational state), (S. Leibowitz and B. G. Hoebel. In: *The Handbook of Obesity*, Bray et al., Eds. Marcel Dekker Inc. (2001)), panic/anxiety-related disorders (S. Rotzinger and F J. P. Vaccarino. *J. Psychiatry Neurosci.* 28, 171-181 (2003); Zwanzger et al. *Neuropsychopharmacol.* 25, 699-703 (2001)), mood disorders, schizophrenia, Parkinson's Disease, depression, attentional/memory functions (for a review of all dopamine-associated states, see F. Noble et al., *Pharmacological Reviews*, 51, 745-781 (1999)), diabetes mellitus, clogging of feeding tubes such as gastric, jejunal tubes etc., peptic ulcer disease, gastric and duodenal ulcers and various peripheral neuropathies (see L. Manni et al., *Br. J. Pharmacol.* 129, 744-750 (2000)) including cancer (CCK-B receptors are present in not only in over 90% of metastic medullary thyroid cases, but in a high percentage of small cell lung cancers, stromal ovarian, and potentially a variety of other tumors, including gastrointestinal adenocarcinomas, neuroendocrine tumors, and malignant glioma (See generally, L. Manni et al., *Br. J. Pharmacol.* 129, 744-750 (2000); M. Behe and T M Behr, *Biopolymers* 66, 399-418 (2002)).

According to one embodiment of this invention, non-pancreatic proteases may be used to control the level of CCK in mammalian blood plasma after the administration of food. In one embodiment, this invention provides a method for treating a CCK-related disease comprising administering to a mammal a therapeutically effective amount of a non-pancreatic protease or a composition comprising a non-pancreatic protease. In an alternate embodiment, this invention provides a method for maintaining or reducing the plasma CCK level in a mammal comprising administering to a mammal a therapeutically effective amount of a non-pancreatic protease or a composition comprising a non-pancreatic protease.

The basal concentration of CCK in blood plasma is typically defined as the concentration of CCK in plasma after overnight fasting. Once a meal or food supplement has been ingested, the CCK concentration in the plasma increases above basal level, resulting in pancreatic stimulation and secretion of pancreatic juice, including enzymes and bicarbonate. One embodiment of this invention relates to maintaining or reducing plasma cholecystokinin (CCK) concentration in a mammal over an extended period of time after food administration.

Similarly, this invention provides methods for significantly reducing the maximum plasma concentration ($C_{max}$) of CCK in a mammal. In one embodiment, this invention relates to a method for reduction of maximum plasma concentration ($C_{max}$) of cholecystokinin (CCK) after administration of food in a mammal comprising the step of administering to said mammal with food a therapeutically effective amount of a non-pancreatic protease or a composition comprising a therapeutically effective amount of non-pancreatic protease, wherein said reduction is measured by comparing (a) said $C_{max}$ in the absence of said protease after food administration to (b) said $C_{max}$ in the presence of said protease after food administration, and wherein said reduction is selected from the group consisting of: (i) at least about 10% to about 25% reduction, (ii) at least about 25% to about 50% reduction, (iii) at least about 50% to about 75% reduction, and (iv) at least about 75% to about 100% reduction. Alternatively, the reduction may be any of at least about a 10%, 20%, 30%, 40%, 50%, 60%, 70%, 80%, 90% or 100% reduction. In a preferred embodiment, the non-pancreatic protease is selected from the group consisting of seaprose, serrapeptase, pronase, a pronase component, or mixtures thereof. In yet another preferred embodiment, the protease is seaprose.

In an alternate embodiment, the methods of this invention relate to treating a CCK-related disease in a mammal by administering to said mammal a therapeutically effective amount of a non-pancreatic protease or a composition comprising a non-pancreatic protease, wherein a plasma cholecystokinin (CCK) level in said mammal after administering said protease is less than or at the same level as the plasma cholecystokinin (CCK) level in said mammal before administering said protease and remains less than or at the same level for a period of time selected from the group consisting of (a) between zero and about 4 hours post-administration, (b) between zero and about 8 hours post-administration; and (c) between zero and about 12 hours post-administration. Alternatively, that period of time may be selected from any of 4, 6, 8, 10 or 12 hours post-administration.

In yet another embodiment, the methods of this invention relate to a reduction of plasma cholecystokinin (CCK) level in said mammal comprising the step of administering to said mammal a therapeutically effective amount of a non-pancreatic protease or a composition comprising a therapeutically effective amount of a non-pancreatic protease.

Methods for Treating Pain in Mammals

This invention also provides methods for treating pain in mammals using a non-pancreatic protease or a composition comprising a non-pancreatic protease. One benefit of such pain treatment is that the active protease agent is not addictive, as are many other pain-reducing agents. Another benefit is that non-pancreatic proteases may be administered non-invasively, a route unavailable with some conventional methods for treating pain, e.g., pain associated with chronic pancreatitis, such as endoscopic placement of stents into the pancreatic duct and intravenous administration of food.

The methods according to this invention may be used to treat a patient suffering from pain associated with pancreatic insufficiency, e.g., pain associated with acute pancreatitis, chronic pancreatitis, cystic fibrosis and post-operative gastrointestinal surgery. One such therapeutic method for treating an individual diagnosed with pancreatitis, for example, comprises selecting an individual suffering from abdominal pain, determining the efficacy of protease administration for treatment of the individual based on a measure of the individual's plasma CCK level administering a non-pancreatic protease to the individual based on the determination of the measure of the individual's CCK level and monitoring the improvement of pain symptoms.

In another aspect, this invention provides methods for treating pain comprising administering to a mammal a therapeutically effective amount of a non-pancreatic protease or a composition comprising a non-pancreatic protease.

Methods for Treating Abdominal Pain in Mammals

As discussed above, food can act as a trypsin-binding substrate to intraluminal trypsin. This in turn prevents trypsin from degrading monitor peptide and intestinal CCK-RF, both of which promote the release of CCK. The increase in CCK subsequently leads to pain.

According to one embodiment of this invention, administration of a non-pancreatic protease to a mammal maintains the basal level of CCK in blood plasma or reduces the CCK level in blood plasma following food ingestion. As a result, the methods of this invention are useful for the treatment of abdominal pain associated with a variety of gastrointestinal diseases and disturbances, including, but not limited to, pancreatitis (acute or chronic), protein malabsorption (azotorrhea), lipid malabsorption (steatorrhea), diabetes mellitus, ulcer disease, and combinations thereof, biliary colic, cholecystitis, ascending cholecystitis, cholelithiasis, narcotic addictions, dysfunction of sphincter of oddi, delayed gastric emptying and chemotherapy damage. The methods of this invention are also useful for CCK antagonism, reduction of hunger and treatment of anorexia.

More particularly, this invention provides methods for treating abdominal pain in a mammal comprising administering to said mammal a therapeutically effective amount of a non-pancreatic protease or a composition comprising a non-pancreatic protease.

As described above, the basal concentration of CCK in plasma is typically defined as the concentration of CCK in plasma in a particular patient or mammal after overnight fasting. Once a meal or food supplement has been ingested or taken in, the CCK concentration in the plasma increases above basal level, resulting in pancreatic stimulation and secretion of pancreatic juice, including enzymes and bicarbonate. One embodiment of this invention relates to maintaining plasma cholecystokinin (CCK) concentrations in a mammal over an extended period of time after food administration.

In one embodiment, the methods of this invention relate to treating abdominal pain in a mammal comprising the step of administering to said mammal a therapeutically effective amount of a non-pancreatic protease or a composition comprising a therapeutically effective amount of a non-pancreatic protease, wherein a plasma cholecystokinin (CCK) level in said mammal after administering said protease is less than or at the same level as a plasma cholecystokinin (CCK) level in said mammal before administering said protease and remains less than or at the same level for a period of time selected from the group consisting of (a) between zero and about 4 hours after administering said protease; (b) between zero and about 8 hours after administering said protease; and (c) between zero and about 12 hours after administering said protease. Alternatively, that period of time may be selected from any of 4, 6, 8, 10 or 12 hours post-administration.

This invention also provides methods for significantly reducing the maximum plasma concentration ($C_{max}$) of CCK in a mammal. As used herein, the phrase "maximum plasma concentration ($C_{max}$)" refers to peak plasma concentration measured after administration of food. Accordingly, one embodiment of the invention relates to methods for treating abdominal pain in a mammal comprising administering to said mammal a therapeutically effective amount of a non-pancreatic protease or a composition comprising a non-pancreatic protease, wherein the administration results in a reduction in plasma cholecystokinin (CCK) level in said mammal following said administration.

All of the methods according to this invention may be carried out by administering the non-pancreatic protease or a composition comprising a non-pancreatic protease to the mammal with or without food. In this, as well as other methods of the invention, administration of the non-pancreatic protease or a composition comprising a non-pancreatic protease with food includes administration of food currently with or subsequent to non-pancreatic protease administration at each meal, beginning in the middle of the meal or alternatively, at the end of the meal, either once or two or three times per meal. Other embodiments of this invention relate to methods for treating abdominal pain in a mammal comprising administering to said mammal with or without food a therapeutically effective amount of a non-pancreatic protease or a composition comprising a non-pancreatic protease, wherein said protease reduces the maximum plasma concentration ($C_{max}$) of CCK in said mammal as compared to the $C_{max}$ of CCK in said mammal without said protease being present during administration of food.

In yet another embodiment, this invention relates to methods for treating abdominal pain in a mammal comprising the step of administering to said mammal a therapeutically effective amount of a non-pancreatic protease or a composition comprising a therapeutically effective amount of a non-pancreatic protease, wherein said protease causes a reduction in maximum plasma concentration ($C_{max}$) of cholecystokinin (CCK) in said mammal, wherein said reduction is measured by comparing (a) said $C_{max}$ in the absence of said protease after food administration to (b) said $C_{max}$ in the presence of said protease after food administration, and wherein said reduction is selected from the group consisting of (i) at least about 10% to about 25% reduction; (ii) at least about 25% to about 50% reduction; (iii) at least about 50% to about 75% reduction; and (iv) at least about 75% to about 100% reduction. That reduction may also be at least about 10% to about 100% reduction. Alternatively, that reduction may be any of at least about a 10%, 20%, 30%, 40%, 50%, 60%, 70%, 80%, 90% or 100% reduction.

Methods of Treating Anorexia in Mammals

Following ingestion of food, elevated CCK levels create the feeling of satiety. By maintaining a reduced CCK plasma level, the methods according to this invention may be used to treating anorexia. Similarly, the methods according to this invention may be used to treat malnutrition. In one embodiment, this invention provides a method for treating anorexia in a mammal comprising administering to said mammal a therapeutically effective amount of a non-pancreatic protease or a composition comprising a therapeutically effect amount of a non-pancreatic protease.

Dosage Forms of Non-Pancreatic Proteases

Any of the methods according to this invention may be carried out using a non-enterically coated, non-pancreatic protease tablet, containing no acid-suppressing agent.

In one embodiment, the methods of this invention relate to the use of a non-enterically coated, non-pancreatic protease tablet, containing no acid-suppressing agent, for the treatment of pain, preferably abdominal pain that is associated with pancreatic insufficiency, and anorexia. In an another embodiment, the methods of this invention relate to use of a non-enterically coated, non-pancreatic protease tablet, containing no acid-suppressing agents, for the reduction of cholescystokinin (CCK) levels after food administration to a basal level that is measured prior to food administration.

In one embodiment according to this invention, the non-pancreatic protease tablet is administered to a mammal at a dose of between one and six tablets, preferably between one and two tablets, most preferably at one tablet, per meal, wherein the tablet comprises an active protease level of between about 20 mg to about 500 mg. In another embodiment, the non-pancreatic protease tablet according to this invention is administered to a mammal at a dose of between one and six tablets, preferably between one and two tablets, most preferably at one tablet, per meal, wherein the tablet comprises an active protease level of between about 50 mg to about 500 mg. Alternatively, the non-pancreatic protease tablet is administered to a mammal at a dose of between one and six tablets, preferably between one and two tablets, most preferably at one tablet, per meal, wherein the tablet comprises an active non-pancreatic protease level of between about 50 mg to about 250 mg.

Alternatively, non-pancreatic active protease is administered to a mammal as one or more tablets providing an active protease dose per meal that is between about 1 mg per kg mammal and 10 mg per kg mammal, preferably between about 1 mg per kg mammal and 3 mg per kg mammal or between about 1 mg per kg mammal and 2 mg per kg mammal.

In order that this invention may be better understood, the following examples are set forth. These examples are for the purpose of illustration only and are not to be construed as limiting the scope of the invention in any manner.

EXAMPLES

The following materials were used in the examples set forth below.

Materials

Commercially-available raw seaprose (SAP) powder (CAS#9074-07-1), derived from Aspergillus melleus, was obtained from Amano Enzyme Inc., Japan (Nagoya, Japan). SAP may be prepared by either a liquid or a solid fermentation process. SAP powder used in the examples herein invention was prepared by solid fermentation. Sodium carbonate, sodium bicarbonate, sodium acetate, sodium phosphate monobasic, sodium phosphate dibasic and potassium phosphate were obtained from Sigma Chemicals (St. Louis, Mo.). Methanol, trifluoroacetic acid and acetonitrile were obtained from Fisher Scientific (Pittsburgh, Pa.) and glutaraldehyde was obtained from Aldrich (Milwaukee, Wis.). Water for Injection (WFI) or United States Pharmacopeia (USP) purified water was used for all buffers and protease solutions. Laboratory chow diet was obtained from Harlan Teklad. Sprague-Dawley rats were obtained from Charles River Laboratories (Raleigh, N.C.). Ketamine and xylazine were obtained from Henry Schein. Casein (Cat. No. C-5890), trypsin (Cat. No. T-7309) and soybean trypsin inhibitor (SBTI, Cat. No. T-9003) were obtained from Sigma Chemicals (St. Louis, Mo.). Creon.RTM.-20 (Solvay Pharmaceuticals, Hannover, Germany) and Viokase.RTM.-8 (Axcan Scandipharm, Inc., Birmingham, Ala.) were purchased from a local pharmacy. CCK-releasing peptide, LCRF.sub.1-35 (A. W. Spannagel, et al., Regulatory Peptides 73, 161-164 (1998); A. W. Spannagel, et al., *Proc. Natl. Acad. Sci.* 93, 4415-4420 (1996)), was obtained from PepScan, Netherlands and Serratiopeptidase was obtained from Specialty Enzymes and Biochemicals Co., Chino, Calif. (Cat. No. B-03 1875, CAS 903 1-94-1). Pronase from Streptomyces griseus was purchased from BioChemika/Fluka Chemical Corp., Milwaukee, Wis. (Cat. No. 81748). Ensure , high protein (24%) with vanilla flavor was purchased from local Pharmacy. Microcrystalline cellulose 103 was obtained from FMC International C. Ireland. Cospovidone XL was obtained from ISP Technologies Inc. Wayne, N.J. Col. Silicon dioxide was obtained from Degussa Corporation, Parsippany, N.J. Talc was obtained from Luzenac America Inc. Englewood, Colo. Magnesium stearate NO-BOy was obtained from Mallinckrodt Baker Inc. Phillipsburg, N.J. Anhydrous Encompress was obtained from Penwest Pharmaceuticals, Cedar Rapids, Iowa.

Conditions for Enzyme Preparation for In Vitro Hydrolysis of CCK-Rel Easing Peptide Seaprose (pH 6.0). Using a volumetric flask, 10 mg of seaprose was dissolved in sodium phosphate buffer (25 mM, pH 6.0) to a final volume of 10 ml, yielding a solution having a final concentration of 1 mg/ml (1400 U/ml). Next, sodium phosphate buffer (25 mM, pH 6.0) was added to 1 ml of the 1 mg/ml (1400 U) solution in a volumetric flask to yield a final volume of 100 ml and a final concentration of 0.01 mg/ml (14 U/ml). Sodium phosphate buffer (25 mM, pH 6.0) was then added to 1.07 ml of the 0.01 mg/ml (14 U/ml) solution in a volumetric flask to yield a final volume of 10 ml and a final concentration of 1.5 U/ml. Finally, 225 µl of 1 mg/ml solution of CCK-releasing peptide, $LCRF_{1-35}$, in sodium phosphate buffer (25 mM, pH 6.0) was mixed with 25 µl of 1.5 U/ml seaprose (0.15 U final) and incubated at 37° C. for various time intervals.

Seaprose (pH 4.5). Using a volumetric flask, 10 mg of seaprose was dissolved in sodium acetate buffer (25 mM, pH 4.5) to a final volume of 10 ml, yielding a solution having a final concentration of 1 mg/ml (1400 U/ml). Next, sodium acetate buffer (25 mM, pH 4.5) was added to 1 ml of the 1 mg/ml (1400 U/ml) solution in a volumetric flask to yield a final volume of 100 ml and a final concentration of 0.01 mg/ml (14 U/ml). Sodium acetate buffer (25 mM, pH 4.5) was then added to 2.5 ml of the 0.01 mg/ml (14 U/ml) solution in a volumetric flask to yield a final volume of 10 ml and a final concentration of 3.5 U/ml. Finally, 225 µl of 1 mg/ml solution of CCK-releasing peptide, $LCRF_{1-35}$, in sodium acetate (25 mM, pH 4.5) was mixed with 25 µl of 3.5 U/ml seaprose (0.35 U final) and incubated at 37° C. for various time intervals.

Serratiopeptidase (pH 6.0). Using a volumetric flask, 10 mg of serratiopeptidase was dissolved in sodium phosphate buffer (25 mM, pH 6.0) to a final volume of 10 ml, yielding a solution having a final concentration of 1 mg/ml (1250 U/ml). Next, sodium phosphate buffer (25 mM, pH 6.0) was added to 1 ml of the 1 mg/ml (1250 U/ml) solution in a volumetric flask to yield a final volume of 100 ml and a final concentration of 0.01 mg/ml (12.5 U/ml). Sodium phosphate buffer (25 mM, pH 6.0) was then added to 1.2 ml of the 0.01 mg/ml (12.5 U/ml) solution in a volumetric flask to yield a final volume of 10 ml and a final concentration of 1.5 U/ml. Finally, 225 µl of 1 mg/ml solution of CCK-releasing peptide, $LCRF_{1-35}$, in sodium phosphate buffer (25 mM, pH 6.0) was mixed with 25 µl of 1.5 U/ml serratiopeptidase (0.15 U final) and incubated at 37° C. for various time intervals.

Serratiopeptidase (pH 4.5). Using a volumetric flask, 10 mg of serratiopeptidase was dissolved in sodium acetate buffer (25 mM, pH 4.5) to a final volume of 10 ml, yielding a solution having a final concentration of 1 mg/ml (1250 U/ml). Next, sodium acetate buffer (25 mM, pH 4.5) was added to 1 ml of the 1 mg/ml (1400 U/ml) solution in a volumetric flask to yield a final volume of 100 ml and a final concentration of 0.01 mg/ml (12.5 U/ml). Sodium acetate buffer (25 mM, pH 4.5) was then added to 2.8 ml of the 0.01 mg/ml (12.5 U/ml) solution in a volumetric flask to yield a final volume of 10 ml and a final concentration of 3.5 U/ml. Finally, 225 µl of 1 mg/ml solution of CCK-releasing peptide, $LCRF_{1-35}$, in sodium acetate buffer (25 mM, pH 4.5) was mixed with 25 µl of 3.5 U/ml serratiopeptidase (0.35 U final) and incubated at 37° C. for various time intervals.

Pronase (pH 6.0). Using a volumetric flask, 10 mg of pronase was dissolved in sodium phosphate buffer (25 mM, pH 6.0) to a final volume of 10 ml, yielding a solution having a final concentration of 1 mg/ml (1000 U/ml). Next, sodium phosphate buffer (25 mM, pH 6.0) was added to 1 ml of the 1 mg/ml (1000 U/ml) solution in a volumetric flask to yield a final volume of 100 ml and a final concentration of 0.01 mg/ml (10 U/ml). Sodium phosphate buffer (25 mM, pH 6.0) was then added to 1.5 ml of the 0.01 mg/ml (10 U/ml) solution in a volumetric flask to yield a final volume of 10 ml and a final concentration of 1.5 U/ml. Finally, 225 µl of 1 mg/ml solution of CCK-releasing peptide, $LCRF_{1-35}$, in sodium phosphate buffer (25 mM, pH 6.0) was mixed with 25 µl of 1.5 U/ml pronase (0.15 U final) and incubated at 37° C. for various time intervals.

Pronase (pH 4.5). Using a volumetric flask, 10 mg of pronase was dissolved in sodium acetate buffer (25 mM, pH 4.5) to a final volume of 10 ml, yielding a solution having a final concentration of 1 mg/ml (1000 U/ml). Next, sodium acetate buffer (25 mM, pH 4.5) was added to 1 ml of the 1 mg/ml (1000 U/ml) solution in a volumetric flask to yield a final volume of 100 ml and a final concentration of 0.01 mg/ml (10 U/ml). Sodium acetate buffer (25 mM, pH 4.5) was then added to 3.5 ml of the 0.01 mg/ml (10 U/ml) solution in a volumetric flask to yield a final volume of 10 ml and a final concentration of 3.5 U/ml. Finally, 225 µl of 1 mg/ml solution of CCK-releasing peptide, $LCRF_{1-35}$, in sodium acetate buffer (25 mM, pH 4.5) was mixed with 25 µl of 3.5 U/ml pronase (0.35 U final) and incubated at 37° C. for various time intervals.

Viokase-8 (pH 6.0). Using a volumetric flask, 10 mg of Viokase-8 was dissolved in sodium phosphate buffer (25 mM, pH 6.0) to a final volume of 10 ml, yielding a solution having a final concentration of 1 mg/ml (120 U/ml). Next, sodium phosphate buffer (25 mM, pH 6.0) was added to 0.125 ml of the 1 mg/ml (120 U/ml) solution in a volumetric flask to yield a final volume of 10 ml and a final concentration of 1.5 U/ml. Finally, 225 µl of 1 mg/ml solution of CCK-releasing peptide, $LCRF_{1-35}$, in sodium phosphate buffer (25 mM, pH 6.0) was mixed with 25 µl of 1.5 U/ml Viokase-8 (0.15 U final) and incubated at 37° C. for various time intervals.

Viokase-8 (pH 4.5). Using a volumetric flask, 10 mg of Viokase-8 was dissolved in sodium acetate buffer (25 mM, pH 4.5) to a final volume of 10 ml, yielding a solution having a final concentration of 1 mg/ml (120 U/ml). Next, sodium acetate buffer (25 mM, pH 4.5) was added to 0.292 ml of the 1 mg/ml (120 U/ml) solution in a volumetric flask to yield a final volume of 10 ml and a final concentration of 3.5 U/ml. Finally, 225 µl of 1 mg/ml solution of CCK-releasing peptide, $LCRF_{1-35}$, in sodium acetate buffer (25 mM, pH 4.5) was mixed with 25 µl of 3.5 U/ml Viokase-8 (0.35 U final) and incubated at 37° C. for various time intervals.

Trypsin (pH 6.0). Using a volumetric flask, 10 mg of trypsin was dissolved in sodium phosphate buffer (25 mM, pH 6.0) to a final volume of 10 ml, yielding a solution having a final concentration of 1 mg/ml (1130 U/ml). Next, sodium phosphate buffer (25 mM, pH 6.0) was added to 0.442 ml of the 1 mg/ml (1130 U/ml) solution in a volumetric flask to yield a final volume of 10 ml and a final concentration of 50 U/ml. Finally, 225 µl of 1 mg/ml solution of CCK-releasing peptide, $LCRF_{1-35}$, in sodium phosphate buffer (25 mM, pH 6.0) was mixed with 25 µl of 50 U/ml trypsin (5 U final) and incubated at 37° C. for various time intervals.

Trypsin (pH 4.5). Using a volumetric flask, 10 mg of trypsin was dissolved in sodium acetate buffer (25 mM, pH 4.5) to a final volume of 10 ml, yielding a solution having a final concentration of 1 mg/ml (1130 U/ml). Next, sodium acetate buffer (25 mM, pH 4.5) was added to 0.442 ml of the 1 mg/ml (1130 U/ml) solution in a volumetric flask to yield a final volume of 10 ml and a final concentration of 50 U/ml. Finally, 225 µl of 1 mg/ml solution of CCK-releasing peptide, $LCRF_{1-35}$, in sodium acetate buffer (25 mM, pH 4.5) was mixed with 25 µl of 50 U/ml trypsin (5 U final) and incubated at 37° C. for various time intervals.

Analytical Techniques and Assays

UV-VIS absorption and Optical Microscopy. UV-VIS spectrophotographs were obtained on a Beckman DU 7400 spectrophotometer, Beckman Coulter Inc., Fullerton, Calif. Optical micrographs were obtained by bright field imaging using an Olympus BX-51 microscope and captured by a Sony DXC-970MD 3CCD color digital video camera using Image-Pro software, Media Cybernetics L.P., Silver Springs, Md., under the magnifications of 40× to 400×.

Reversed-Phase HPLC. The digested/hydrolyzed peptides of the CCK-releasing peptide were separated with a Agilent 1100 HPLC system equipped with computer interface and software (Agilent Chemstation software) for automatic integration and analysis of chromatographic peaks. A Discovery C18 reversed-phase column (100×2.1 mm, 3 µm) from Supelco was used to separate the digested peptides. Linear gradient elution of peptides (monitored at 214 nm and 280 nm) was achieved using a solvent system composed of 0.1% trifluoroacetic acid (TFA) in water (solvent A) and 0.08% TFA in acetonitrile (solvent B) and with a flow rate of 0.25 ml/min at 30° C. The gradient elution was as follows: 0-3 min 0% buffer B), 3-38 min (0-70% buffer B), 38-40 min (70% buffer B) and 40-40.5 min (70-0% buffer B).

CCK Purification. Sep-Pak Vac 3 cc (500 mg) cartridges were inserted onto an extraction manifold and conditioned with 15 ml 100% methanol. Columns were equilibrated with 15 ml 0.1% trifluoroacetic acid (TFA) in $H_2O$ and labeled conical centrifuge tubes were inserted into the extraction manifold to collect the load/wash eluent from cartridges. Blood plasma samples were then immediately loaded after collection from rats in order to prevent degradation of CCK. Contaminants were washed from the column with TFA in $H_2O$. Labeled conical centrifuge tubes in the extraction manifold collected the CCK-containing eluent from each Sep-Pak cartridge and the CCK was slowly eluted (flow rate <1 ml/min) from the column with TFA in acetonitrile. Once the elution was completed, tubes were capped and frozen on dry ice. Contents were lyophilized for 24-48 hours using a freeze dryer and stored at −80° C. until use.

Example 1

Crystallization of seaprose. Raw seaprose powder (100 g, approximately 70% pure) was dissolved in 1000 ml of 10 mM sodium carbonate, pH 9.50. The resulting seaprose solution was then sterile filtered in a hood by passing it through a 0.22 µm filter (Nalgene). The solution was stirred overnight on a magnetic stirrer at 4° C. The following day, the resulting crystals were separated from the solution by centrifuging at 2,000 rpm (Beckman centrifuge Model GS-6R with GH 3.8 swinging bucket rotor) for 20 minutes and the supernatant was subsequently removed. Crystals were again washed with a minimum volume (80 ml) of 10 mM sodium carbonate, pH 9.50 and re-centrifuged at 3,000 rpm for 20 minutes. The wash supernatant was then removed and the crystals were re-suspended in a total volume of 1.2 L (10 mM sodium carbonate, pH 9.5), $AbS_{280}$=34 mg/ml, and a milky solution formed. The re-dissolved crystals were allowed to stand for 2-3 days at 4° C. for additional re-crystallization. The final yield of the purified seaprose crystals was 44% (see FIG. 1).

Example 2

Crosslinking of seaprose crystals. Crosslinking was carried out using glutaraldehyde (final concentration of 1%). Twenty mls of seaprose crystals, as prepared above, (20 mg/ml in 10 mM sodium carbonate, pH 9.5) was treated with 800 µl of 25% glutaraldehyde solution for 24 hours at 4° C. with tumbling. The crosslinked crystal solution was concentrated to a final concentration of 20-25 mg/ml under sterile conditions. After 24 hours, the crystals were centrifuged and washed (5×) with 10 mM Tris buffer, pH 7.0.

Example 3

Figure 2:
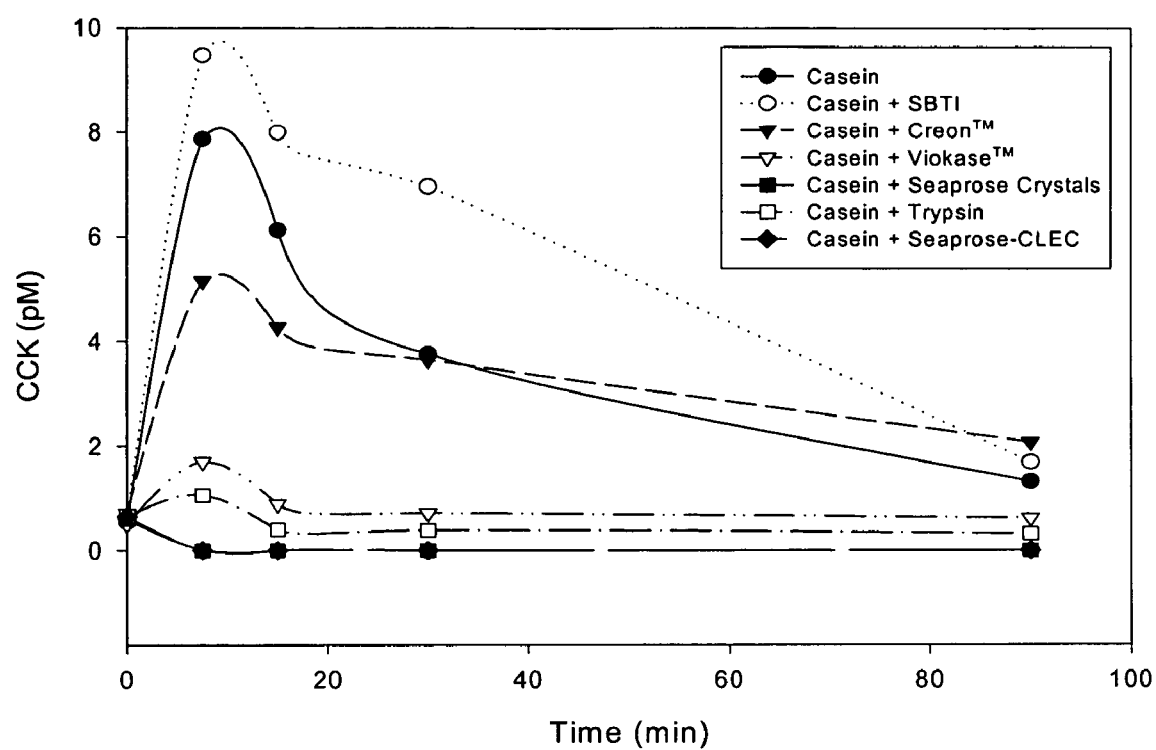
FIG. 2 illustrates CCK levels in blood plasma of rats measured by CCK radioimmunoassay ("RIA") in response to diets containing various exogenous enzyme supplementations. See Example 3.

Plasma CCK response to diet with various exogenous enzyme supplementations in rats. Rats, each weighing approximately 350 grams, that had been conventionally group-housed and given access to water and laboratory chow ad libitum were randomly divided into eight treatment groups and further subdivided into five cohorts, and each cohort had three rats. All rats were fasted overnight (20-22 hr) and the next morning (between 7-9 am) were orally administered, post-operative (PO), 5 ml of liquid into the stomach via a feeding needle attached to an orogastric tube. The 5 ml aliquots were prepared from components shown below for groups 1-8. For example, the treatment for group 1, vehicle, contained 5 ml of water, group 2, Casein control, contained 900 mg casein in water to yield a final volume of 5 ml, group 3, Casein+seaprose crystals, contained 900 mg casein plus 144 mg (201,600 USP units) of seaprose crystals in water, group 4, Casein+trypsin, contained 900 mg casein plus 1000 mg (1,250,000 USP units) of trypsin in water, group 5, Casein+crosslinked seaprose crystals contained 900 mg casein plus 294 mg (201,600 USP units) of crosslinked seaprose crystals in water, group 6, Casein+Soyabean trypsin inhibitor contained 900 mg casein plus 2 mg of Soyabean trypsin inhibitor in water, group 7, Casein+Creon®-20 contained 900 mg casein plus 1000 mg (201,038 USP units) of Creon®-20 in water, and group 8, Casein+Viokase®-8 contained 900 mg casein plus 1000 mg (104,500 USP units) of Viokase®-8 in water. Rats were then given an intraperitoneal (ip) overdose of 1 ml of ketamine:xylezine (mixture of 10 ml ketamine (100 mg) and 1 ml xylezine (100 mg)) as an anesthesia, the thoracic cavity was opened, and blood was drawn via cardiac puncture of the right ventricle. Plasma samples were obtained from each rat using a 10 cc syringe (16 gauge) and collected in heparinized blood tubes during perfusion at the following 5 time points (see Table 3): pre-treatment (fasted), 7.5, 15, 30, and 90 min post-test formulation administration. The plasma samples were separated by centrifugation (10 min, 3000 rpm at 4° C.) and decanted into cryotubes. CCK was then purified from plasma using Sep-Pak cartridges, as described above. CCK levels were measured by competitive radioimmunoassay (RIA) using a highly specific antiserum raised against CCK-8 sulphate (<0.5% cross-reactivity to gastrin-17) and $I^{125}$ as a tracer (CCK RIA kit from Euro-Diagnostica). Changes in CCK levels in plasma over time following orogastric feeding of the various dietary liquids are presented in Table 3 and FIG. 2. Lowest levels (i.e., the greatest suppression) of CCK occurred in both groups treated with seaprose in the test formulations.

ml of liquid into the stomach via a feeding needle attached to an orogastric tube. The 5 ml aliquots were prepared from components shown below for groups 1-6. For example, treatment for group 1, Vehicle, contained 5 ml of water, group 2, Ensure® control, contained 5 ml of Ensure®, group 3 contained 143 mg or 200,000 USP units of seaprose crystals in Ensure® to yield a final volume of 5 ml, group 4 contained 57 mg or 80,000 USP units of seaprose crystals in Ensure® to yield a final volume of 5 ml, group 5 contained 14 mg or 20,000 USP units of seaprose crystals in Ensure® to yield a final volume of 5 ml, and group 6 contained 3.6 mg or 5,000 USP units of seaprose crystals in Ensure® to yield a final volume of 5 ml. Rats were then given an overdose (ip) of 1 ml ketamine:xylezine (as in Example 3) and trunk blood was collected into heparin-coated tubes during perfusion at the following 6 time points (see Table 4): pre-treatment [fasted], 7.5, 15, 30, 60, and 90 min post-test formulation administration. Plasma samples were then collected from each rat by using a 10 cc syringe (16 gauge) and collected in heparinized blood tubes. The plasma samples were separated by centrifugation (10 min, 3000 rpm at 4° C.) and decanted into cryotubes. Plasma samples were then processed onto Sep-Pak

TABLE 3

CCK Levels in Plasma

| Time (min) | Control Vehicle (water) | Casein | Casein + Seaprose Crystals | Casein + Trypsin | Casein + Seaprose Cross-linked Crystals | Casein + SBTI | Casein + Creon ® | Casein + Viokase ® |
|---|---|---|---|---|---|---|---|---|
| | | | | Concentration of CCK in Plasma (pM) | | | | |
| 0 | 0.18 | 0.47 | 0.64 | 0.72 | 0.66 | 0.89 | 0.72 | 0.53 |
| | 0.17 | 0.62 | 0.73 | 0.69 | 0.58 | 0.42 | 0.88 | 0.56 |
| | 0.26 | 0.55 | 0.42 | 0.57 | 0.71 | 0.45 | 0.53 | 0.44 |
| | 0.20* | 0.55* | 0.60* | 0.66* | 0.65* | 0.59* | 0.71* | 0.51* |
| 7.5 | 0.77 | 8.84 | 0 | 1.06 | 0 | 9.55 | 5.20 | 1.88 |
| | 0.84 | 7.61 | 0 | 1.22 | 0 | 8.76 | 5.71 | 1.67 |
| | 0.87 | 7.13 | 0 | 0.89 | 0 | 10.1 | 4.55 | 1.55 |
| | 0.83* | 7.86* | 0* | 1.06* | 0* | 9.47* | 5.15* | 1.70* |
| 15 | 0.12 | 6.6 | 0 | 0.47 | 0 | 6.56 | 4.33 | 0.89 |
| | 0.23 | 5.44 | 0 | 0.39 | 0 | 9.43 | 3.87 | 0.76 |
| | 0.32 | 6.32 | 0 | 0.33 | 0 | 7.97 | 4.62 | 1.02 |
| | 0.22* | 6.12* | 0* | 0.40* | 0* | 7.99* | 4.27* | 0.89* |
| 30 | 0.11 | 3.88 | 0 | 0.35 | 0 | 6.10 | 3.94 | 0.77 |
| | 0.21 | 3.23 | 0 | 0.44 | 0 | 7.88 | 3.13 | 0.68 |
| | 0.00 | 4.17 | 0 | 0.37 | 0 | 6.74 | 3.88 | 0.71 |
| | 0.11* | 3.76* | 0* | 0.39* | 0* | 6.96* | 3.65* | 0.72* |
| 90 | 0.00 | 1.22 | 0 | 0.31 | 0 | 2.16 | 2.31 | 0.68 |
| | 0.00 | 1.75 | 0 | 0.34 | 0 | 1.57 | 2.11 | 0.55 |
| | 0.19 | 0.98 | 0 | 0.32 | 0 | 1.33 | 1.78 | 0.63 |
| | 0.06* | 1.32* | 0* | 0.32* | 0* | 1.69* | 2.07* | 0.62* |

*Average value of CCK concentration reported for each of three rats per cohort. Rats in this study were randomly divided into eight treatment groups and further subdivided into five cohorts, with three rats in each cohort.

Example 4

Figure 3:
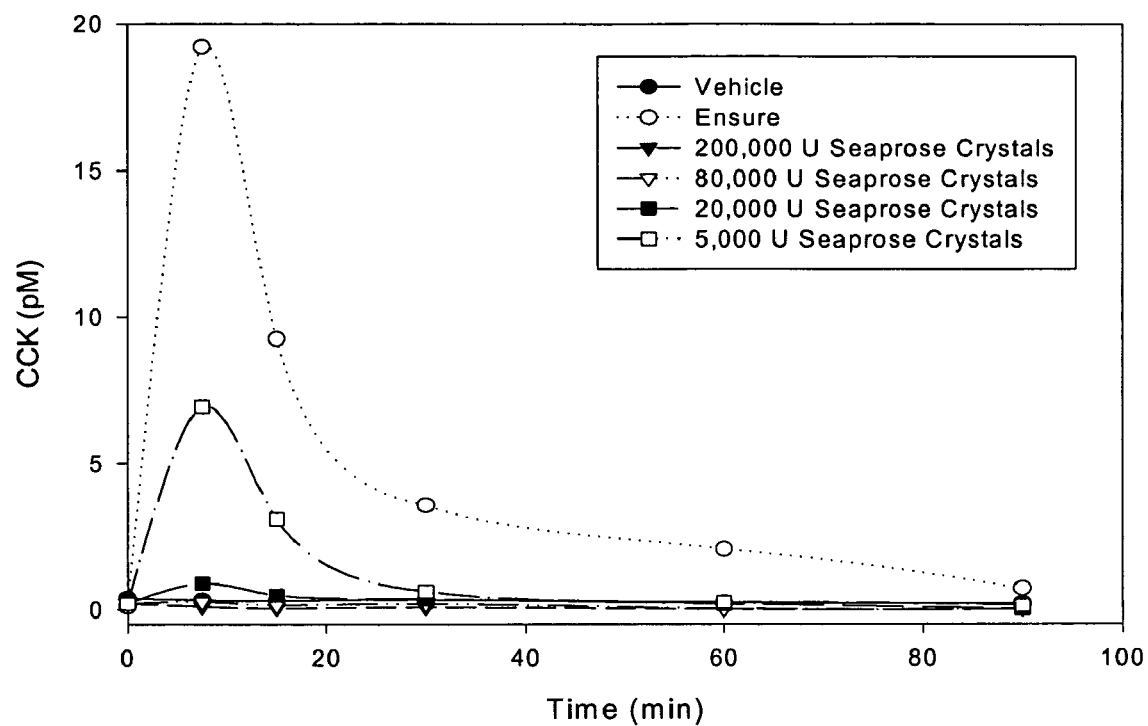
FIG. 3 illustrates CCK levels in blood plasma of rats measured by CCK radioimmunoassay ("RIA") in response to diets containing exogenous seaprose crystal supplementations. See Example 4.

Plasma CCK response to diet with various exogenous enzyme supplementations in rats. Rats, each weighing approximately 350 grams, that had been conventionally group-housed and given access to water and laboratory chow ad libitum were randomly divided into six treatment groups and further divided into six cohorts and each cohort had three rats. All rats were fasted overnight (20-22 hr) and the next morning (between 7-9 am) were orally administered (PO) 5 cartridges as described above. CCK levels were measured by competitive RIA using a highly specific antiserum raised against CCK-8 sulphate (<0.5% cross-reactivity to gastrin-17) and $I^{125}$ as a tracer (CCK RIA kit from Euro-Diagnostica). Changes in CCK levels in plasma over time following orogastric feeding of the various dietary liquids are presented in Table 4 and FIG. 3. Lower levels (i.e., greater suppression) of CCK were evident in those groups treated with higher doses of seaprose crystals in the test formulations.

TABLE 4

CCK Levels in Plasma

| Time (min) | Control Vehicle (water) | Ensure ® | Ensure ® + Seaprose 200,000 U | Ensure ® + Seaprose 80,000 U | Ensure ® + Seaprose 20,000 U | Ensure ® + Seaprose 5,000 U |
|---|---|---|---|---|---|---|
| | | | Concentration of CCK in Plasma (pM) | | | |
| 0 | 0.342 | 0.000 | 0.362 | 0.362 | 0.362 | 0.362 |
| | 0.366 | 0.030 | 0.151 | 0.151 | 0.151 | 0.151 |
| | 0.439 | 0.270 | 0.100 | 0.100 | 0.100 | 0.100 |
| | 0.382* | 0.098* | 0.204* | 0.204* | 0.204* | 0.204* |
| 7.5 | 0.274 | 16.920 | 0.149 | 0.322 | 0.937 | 7.014 |
| | 0.418 | 20.510 | 0.141 | 0.341 | 0.837 | 6.630 |
| | 0.288 | 20.200 | 0.000 | 0.128 | 0.913 | 7.176 |
| | 0.327* | 19.211* | 0.096* | 0.264* | 0.896* | 6.940* |
| 15 | 0.238 | 6.900 | 0.083 | 0.129 | 0.466 | 4.042 |
| | 0.398 | 9.420 | 0.023 | 0.157 | 0.429 | 3.104 |
| | 0.274 | 11.430 | 0.000 | 0.146 | 0.556 | 2.149 |
| | 0.303* | 9.247* | 0.035* | 0.144* | 0.484* | 3.098* |
| 30 | 0.240 | 2.532 | 0.069 | 0.172 | 0.378 | 0.612 |
| | 0.425 | 4.704 | 0.070 | 0.161 | 0.323 | 0.604 |
| | 0.335 | 3.463 | 0.064 | 0.249 | 0.353 | 0.639 |
| | 0.333* | 3.567* | 0.068* | 0.194* | 0.351* | 0.618* |
| 60 | 0.201 | 1.578 | 0.013 | 0.018 | 0.280 | 0.344 |
| | 0.219 | 1.996 | 0.000 | 0.032 | 0.145 | 0.208 |
| | 0.290 | 2.624 | 0.000 | 0.026 | 0.131 | 0.186 |
| | 0.237* | 2.066* | 0.004* | 0.025* | 0.185* | 0.246* |
| 90 | 0.208 | 0.795 | 0.000 | 0.000 | 0.026 | 0.056 |
| | 0.146 | 0.734 | 0.000 | 0.000 | 0.000 | 0.289 |
| | 0.250 | 0.613 | 0.000 | 0.000 | 0.032 | 0.043 |
| | 0.201* | 0.714* | 0.000* | 0.000* | 0.019* | 0.129* |

*Average value of CCK concentration reported for each of three rats per cohort. Rats in this study were randomly divided into six treatment groups and further subdivided into six cohorts, with three rats in each cohort.

Example 5

Figure 4:
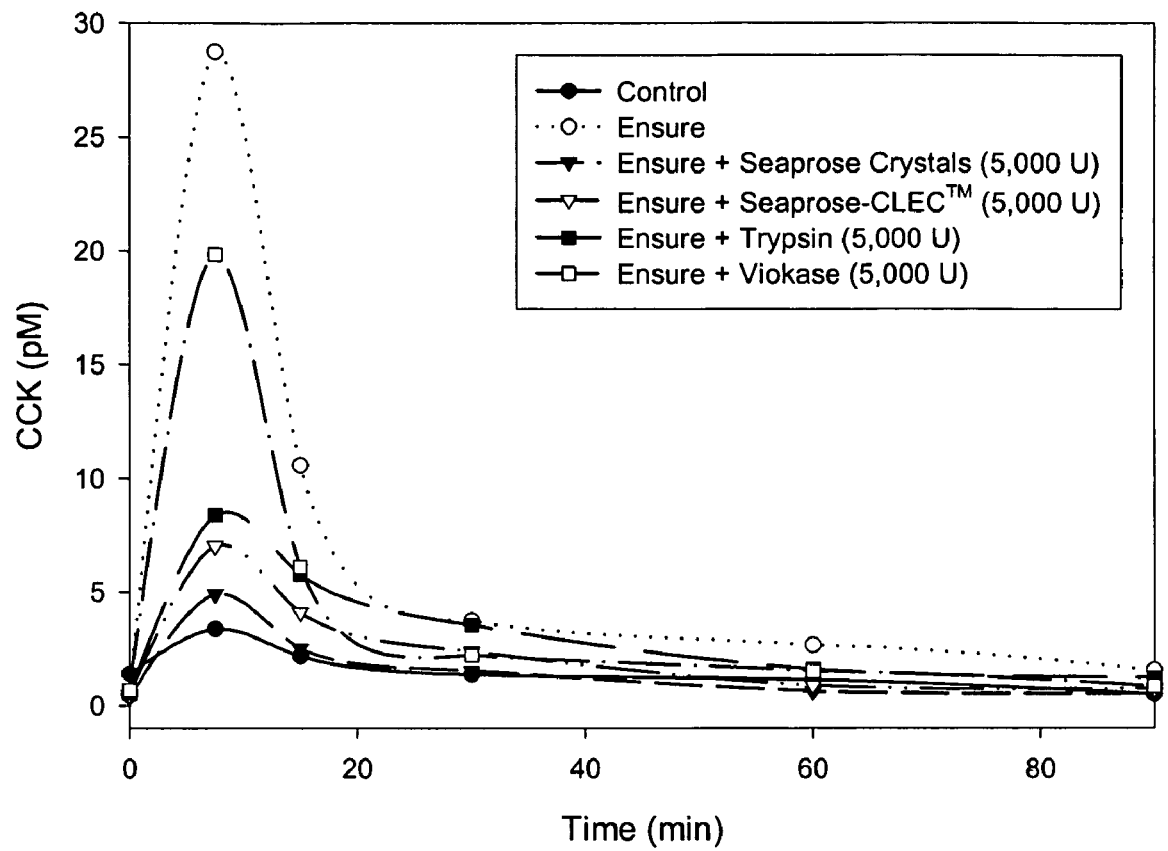
FIG. 4 illustrates CCK levels in blood plasma of rats measured by CCK radioimmunoassay ("RIA") in response to diets containing various exogenous enzyme supplementations. See Example 5.

Plasma CCK response to diet with various exogenous enzyme supplementations in rats. Rats, each weighing approximately 350 grams, that had been conventionally group-housed and given access to water and laboratory chow ad libitum were randomly divided into six treatment groups and further divided into six cohorts and each cohort had three rats. All rats were fasted overnight (20-22 hr) and the next morning (between 7-9 am) were orally administered (PO) 5 ml of liquid into the stomach via a feeding needle attached to an orogastric tube. The 5 ml aliquots were prepared from components shown below in groups 1-6. For example, group 1, Vehicle, contained 5 ml of water, group 2, Ensure® Control, contained 5 ml of Ensure, group 3 contained 3.6 mg or 5,000 USP units of seaprose crystals in Ensure® to yield a final volume of 5 ml, group 4 contained 21 mg or 5,000 USP units of crosslinked seaprose crystals (Seaprose-CLEC) in Ensure® to yield a final volume of 5 ml, group 5 contained 2 mg or 5,000 USP units of trypsin in Ensure® to yield a final volume of 5 ml and group 6 contained 72.3 mg or 5,000 USP units of commercially-available Viokase®-8 in Ensure to yield a final volume of 5 ml. Rats were then given an overdose (ip) of 1 ml ketamine:xylezine (as in Example 3) and trunk (heart) blood was collected into heparin-coated tubes at the following 6 time points (see Table 5): pre-treatment [fasted], 7.5, 15, 30, 60, and 90 min post-test formulation administration. Plasma samples were then collected from each rat by using a 10 cc syringe (16 gauge) and collected in heparinized blood tubes. The plasma samples were separated by centrifugation (10 min, 3000 rpm at 4° C.) and decanted into cryotubes. Plasma samples were then processed onto Sep-Pak cartridges as described above. CCK levels were measured by competitive RIA using a highly specific antiserum raised against CCK-8 sulphate (<0.5% cross-reactivity to gastrin-17) and $I^{125}$ as a tracer (CCK RIA kit from Euro-Diagnostica). Changes in CCK levels in plasma (pmol/L) over time following orogastric feeding of the various dietary liquids are presented in Table 5 and FIG. 4. Lower levels (i.e., greater suppression) of CCK were evident in those groups treated with seaprose crystals in the test formulations when compared to other formulations. For example, the percent reductions in $C_{max}$ were calculated as follows: 0% (Ensure®), 93.92% (Ensure®+seaprose crystals), 85.56% (Ensure®+Seaprose-CLEC), 80.25% (Ensure®+trypsin), and 35.08% (Ensure®+Viokase®-8)

TABLE 5

CCK Levels in Plasma

| Time (min) | Control Vehicle (water) | Ensure ® | Ensure ® + Seaprose Crystals 5,000 U | Ensure ® + Seaprose-CLEC 5,000 U | Ensure ® + Trypsin 5,000 U | Ensure ® + Viokase ® 5,000 U |
|---|---|---|---|---|---|---|
| | | | Concentration of CCK in Plasma (pM) | | | |
| 0 | 1.52 | 0.40 | 0.43 | 0.54 | 0.50 | 0.94 |
| | 1.48 | 0.46 | 0.27 | 0.26 | 0.58 | 0.69 |

TABLE 5-continued

CCK Levels in Plasma

| Time (min) | Control Vehicle (water) | Ensure® | Ensure® + Seaprose Crystals 5,000 U | Ensure® + Seaprose-CLEC 5,000 U | Ensure® + Trypsin 5,000 U | Ensure® + Viokase® 5,000 U |
|---|---|---|---|---|---|---|
| | \multicolumn{6}{c}{Concentration of CCK in Plasma (pM)} | | | | | |
| | 1.15 | 0.43 | 0.30 | 0.61 | 0.49 | 0.41 |
| | 1.39* | 0.43* | 0.34* | 0.47* | 0.53* | 0.68* |
| 7.5 | 1.69 | 30.35 | 5.37 | 5.77 | 6.70 | 18.68 |
| | 5.76 | 31.96 | 5.22 | 6.11 | 7.38 | 13.89 |
| | 2.66 | 23.91 | 4.15 | 9.22 | 11.06 | 26.95 |
| | 3.37* | 28.74* | 4.91* | 7.03* | 8.38* | 19.84* |
| 15 | 1.71 | 13.21 | 2.55 | 4.20 | 4.01 | 9.80 |
| | 2.57 | 9.66 | 2.06 | 5.36 | 6.58 | 5.17 |
| | 2.19 | 8.84 | 2.88 | 2.73 | 6.70 | 3.38 |
| | 2.16* | 10.57* | 2.50* | 4.09* | 5.76* | 6.11* |
| 30 | 1.29 | 3.57 | 2.00 | 1.88 | 3.19 | 2.43 |
| | 1.37 | 4.56 | 1.43 | 3.92 | 5.17 | 1.81 |
| | 1.44 | 3.07 | 1.16 | 1.34 | 2.26 | 2.37 |
| | 1.36* | 3.73* | 1.53* | 2.38* | 3.54* | 2.21* |
| 60 | 1.15 | 2.00 | 0.60 | 1.13 | 1.75 | 1.38 |
| | 1.57 | 3.62 | 0.92 | 0.67 | 1.03 | 0.93 |
| | 0.69 | 2.32 | 0.33 | 0.82 | 1.99 | 2.22 |
| | 1.13* | 2.65* | 0.62* | 0.87* | 1.59* | 1.51* |
| 90 | 0.33 | 2.10 | 0.32 | 0.51 | 1.10 | 1.13 |
| | 0.64 | 0.66 | 0.68 | 0.92 | 1.47 | 1.06 |
| | 0.50 | 1.90 | 0.58 | 0.78 | 1.07 | 0.37 |
| | 0.49* | 1.55* | 0.53* | 0.74* | 1.21* | 0.85* |

*Average value of CCK concentration reported for each of three rats per cohort. Rats in this study were randomly divided into six treatment groups and further subdivided into six cohorts, with three rats in each cohort.

Example 6

Figure 5:
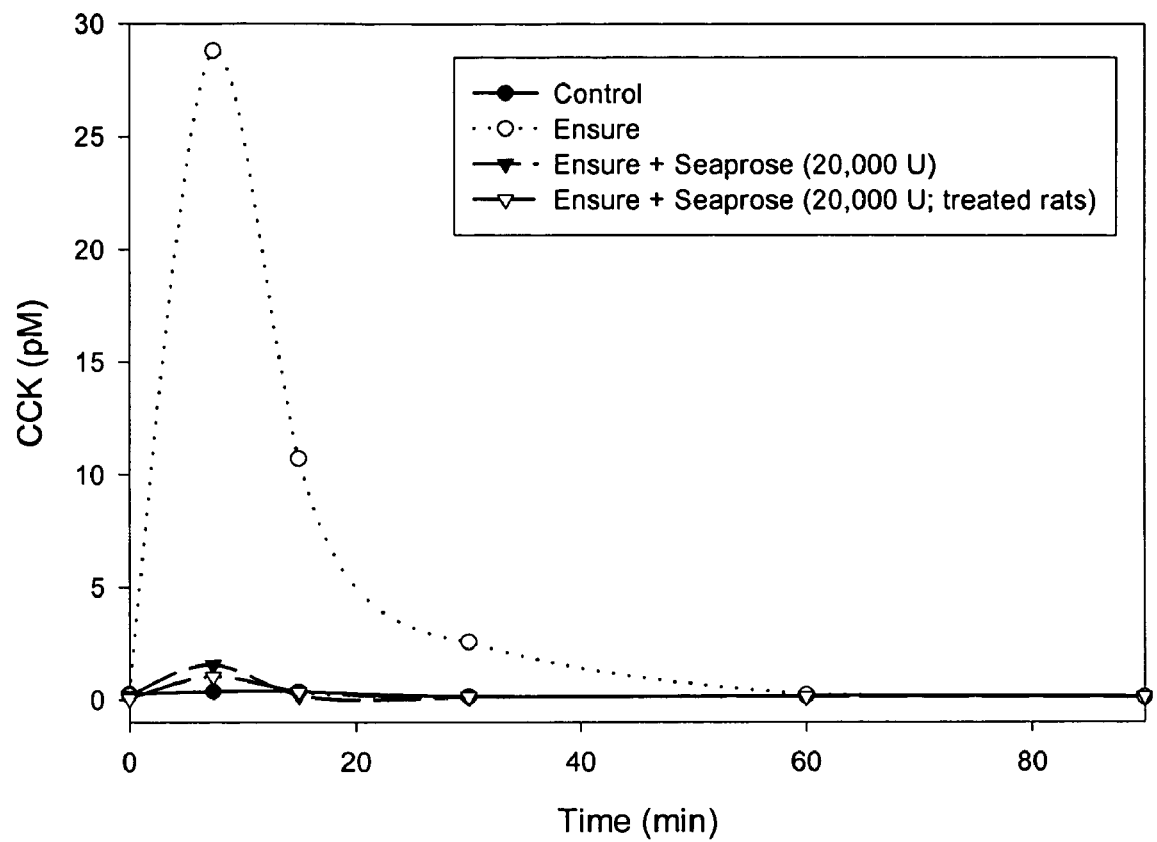
FIG. 5 illustrates CCK levels in blood plasma of rats measured by CCK radioimmunoassay ("RIA") in response to diets containing exogenous seaprose crystal supplementations. See Example 6.

Plasma CCK response to diet with repeated dosing of exogenous enzyme supplementations in rats. Rats, each weighing approximately 350 grams, that had been conventionally group-housed and given access to water and laboratory chow ad libitum were randomly divided into four treatment groups and further divided into six cohorts and each cohort had five rats. All rats were fed a standard chow diet ad libitum for 3 consecutive days. In addition, the group 4 rats were fed 5 ml of Ensure® containing 20,000 USP units seaprose by gavage over these 3 consecutive days (treated rats). All rats were fasted overnight (20-22 hr) and fed 5 ml of the liquid formulation by instillation into the stomach via an orogastric tube between 7-9 am on the fourth day. The 5 ml aliquots were prepared from components shown below for groups 1-4. For example, group 1, Vehicle, contained 5 ml of water, group 2, Ensure® control contained 5 ml of Ensure®, group 3 contained 14 mg or 20,000 USP units of seaprose crystals in Ensure® to yield a final volume of 5 ml, group 4 contained 14 mg or 20,000 USP units of seaprose crystals in Ensure® to yield a final volume of 5 ml (refer to Table 6). Rats were then given an overdose (ip) of 1 ml ketamine:xylezine (as in Example 3) and trunk (heart) blood was collected into heparin-coated tubes at the following 6 time points (see Table 6): pre-treatment [fasted], 7.5, 15, 30, 60, and 90 min post-test formulation administration. Plasma samples were then collected from each rat by using a 10 cc syringe (16 gauge) and collected in heparinized blood tubes. The plasma samples were separated by centrifugation (10 min, 3000 rpm at 4° C.) and decanted into cryotubes. Plasma samples were then processed onto Sep-Pak cartridges as described above. CCK levels were measured by competitive RIA using a highly specific antiserum raised against CCK-8 sulphate (<0.5% cross-reactivity to gastrin-17) and $I^{125}$ as a tracer (CCK RIA kit from Euro-Diagnostica). Changes in CCK levels in plasma over time following orogastric feeding of the various dietary liquids are presented in Table 6 and FIG. 5. Both groups 3 and 4 showed comparable suppression of CCK levels, thus indicating that prior exposure of rats to Seaprose did not change the level of suppression of CCK. For example, the percent reductions in $C_{max}$ were calculated as follows: 0% (Ensure®), 95.83% (Ensure®+seaprose crystals, immediate), and 97.69% (Ensure®+seaprose crystals, repeated).

TABLE 6

CCK Levels in Plasma

| Time (min) | Control Vehicle (water) | Ensure | Ensure + Seaprose 20,000 U | Ensure + Seaprose 20,000 U (Treated rats)‡ |
|---|---|---|---|---|
| | \multicolumn{4}{c}{Concentration of CCK in Plasma (pM)} | | | |
| 0 | 0.00 | 0.05 | 0.00 | 0.22 |
| | 0.82 | 0.00 | 0.04 | 0.00 |
| | 0.34 | 0.37 | 0.00 | 0.00 |
| | 0.00 | 0.00 | 0.33 | 0.00 |
| | 0.15 | 0.42 | 0.50 | 0.00 |
| | 0.26* | 0.17* | 0.17* | 0.04* |
| 7.5 | 0.52 | 26.78 | 1.25 | 1.08 |
| | 0.86 | 26.27 | 2.47 | 0.92 |
| | 0.43 | 26.84 | 0.94 | 1.16 |
| | 0.00 | 29.34 | 1.56 | 0.83 |
| | 0.00 | 34.87 | 1.53 | 1.11 |
| | 0.36* | 28.80* | 1.55* | 1.02* |
| 15 | 0.08 | 12.24 | 0.71 | 0.22 |
| | 0.50 | 12.70 | 0.05 | 0.32 |
| | 0.07 | 15.39 | 0.03 | 0.29 |
| | 0.50 | 7.97 | 0.00 | 0.47 |
| | 0.66 | 5.19 | 0.07 | 0.39 |
| | 0.36* | 10.70* | 0.17* | 0.34* |
| 30 | 0.08 | 3.57 | 0.00 | 0.05 |
| | 0.00 | 1.30 | 0.22 | 0.07 |

TABLE 6-continued

CCK Levels in Plasma

| Time (min) | Control Vehicle (water) | Ensure | Ensure + Seaprose 20,000 U | Ensure + Seaprose 20,000 U (Treated rats)‡ |
|---|---|---|---|---|
| | | Concentration of CCK in Plasma (pM) | | |
| | 0.28 | 4.33 | 0.27 | 0.00 |
| | 0.00 | 2.12 | 0.00 | 0.52 |
| | 0.27 | 1.51 | 0.03 | 0.06 |
| | 0.13* | 2.57* | 0.10* | 0.14* |
| 60 | 0.11 | 0.33 | 0.04 | 0.00 |
| | 0.06 | 0.04 | 0.09 | 0.06 |
| | 0.46 | 0.30 | 0.24 | 0.30 |
| | 0.00 | 0.21 | 0.12 | 0.16 |
| | 0.17 | 0.28 | 0.11 | 0.14 |
| | 0.16* | 0.23* | 0.12* | 0.13* |
| 90 | 0.04 | 0.14 | 0.11 | 0.06 |
| | 0.18 | 0.00 | 0.00 | 0.16 |
| | 0.11 | 0.20 | 0.12 | 0.29 |
| | 0.00 | 0.00 | 0.13 | 0.18 |
| | 0.39 | 0.10 | 0.09 | 0.00 |
| | 0.14* | 0.09* | 0.09* | 0.14* |

**Average value of CCK concentration reported for each of three rats per cohort. Rats in this study were randomly divided into four treatment groups and further subdivided into six cohorts, with three rats in each cohort.
‡The rats in group 4 in addition to normal diet received Ensure and Seaprose (20K) for three days prior to final treatment.

Example 7

In vitro hydrolysis of CCK-releasing peptide with various proteases at pH 6.0. CCK-releasing peptide (1 mg/ml) was suspended in 25 mM sodium phosphate buffer, pH 6.0 and incubated with 0.15 units (USP units) of seaprose (SAP) at 37° C in a water bath (see above Conditions for Enzyme Preparation). At different time intervals (0, 1, 2 and 4 hrs), 10 μl of sample was injected into Agilent 1100 reversed-phase HPLC system and the digested peptides were separated on a C18 reversed-phase column using a gradient elution. The undigested CCK-releasing peptide eluted at 22.8 min. The amount of remaining undigested CCK-releasing peptide after protease digestion was calculated from the area under the peak at 22.8 min and the results are shown in Table 7. Similar CCK hydrolysis assays were done using proteases like serratiopeptidase, pronase, trypsin or Viokase®-8 and the results are presented in Table 7.

TABLE 7

Hydrolysis of CCK-releasing Peptide at pH 6.0

| Protease | Weight | | Percent of CCK-releasing peptide remaining after hydrolysis with protease Time (hr) | | | |
|---|---|---|---|---|---|---|
| | Units | (μg) | 0 | 1 | 2 | 4 |
| Seaprose | 0.15 | 0.100 | 100 | 71 | 46 | 17 |
| Serratiopeptidase | 0.15 | 0.120 | 100 | 74 | 51 | 23 |
| Pronase | 0.15 | 0.150 | 100 | 53 | 33 | 13 |
| Trypsin | 5.00 | 4.40 | 100 | 85 | 73 | 58 |
| Viokase ® | 0.15 | 1.25 | 100 | 81 | 65 | 42 |

At pH 6.0, the fungal/bacterial proteases were more active than either Viokase or trypsin, which are both of pancreatic origin, and hydrolyzed the CCK-releasing peptide faster than either trypsin or Viokase®. Because the fungal/bacterial enzymes have higher specific activity than either Viokase® or trypsin, a smaller amount of such enzymes are needed on a per weight basis to hydrolyze the CCK-releasing peptide than either Viokase® or trypsin.

Example 8

In vitro hydrolysis of CCK-releasing peptide with various proteases at pH 4.5. CCK-releasing peptide (1 mg/ml) was suspended in 25 mM sodium acetate buffer, pH 4.5 and incubated with 0.35 units (USP units) of seaprose (SAP) at 37° C. in a water bath (see above Conditions for Enzyme Preparation). At different time intervals (0, 1, 2 and 4 hrs), 10 μl of sample was injected into Agilent 1100 reversed-phase HPLC system and any digested peptide was separated on a C18 reverse phase column using a gradient elution. The undigested CCK-releasing peptide eluted at 20.6 min. The amount of remaining undigested CCK-releasing peptide after protease digestion was calculated from the area under the peak at 20.6 min and the results are shown in Table 8. Similar CCK hydrolysis experiments were carried out using proteases like serratiopeptidase, pronase, trypsin or Viokase®-8 and the results are presented in Table 8. At pH 4.5, the fungal proteases were more active than either Viokase® or trypsin, which are of pancreatic origin, and hydrolyzed the CCK-releasing peptide faster than either trypsin or Viokase®. Because the fungal enzymes have a higher specific activity than either Viokase® or trypsin, a smaller amount is needed on a per weight basis to hydrolyze the CCK-releasing peptide.

TABLE 8

Hydrolysis of CCK-releasing Peptide at pH 4.5

| Protease | Weight | | Percent of CCK peptide remaining after hydrolysis with protease Time (hr) | | | |
|---|---|---|---|---|---|---|
| | Units | (ug) | 0 | 1 | 2 | 4 |
| Seaprose | 0.35 | 0.223 | 100 | 81 | 71 | 60 |
| Serratiopeptidase | 0.35 | 0.228 | 100 | 88 | 77 | 66 |
| Pronase | 0.35 | 0.350 | 100 | 93 | 89 | 84 |
| Trypsin | 5.00 | 4.40 | 100 | 90 | 81 | 63 |
| Viokase ® | 0.35 | 2.92 | 100 | 94 | 88 | 82 |

Example 9

Determination of protease enzyme activity in the compressed state and feasibility of using compressed protease tablets for treatment of pain. In treating pancreatic pain in humans, the amount of protease per dose per meal will vary depending on the severity of pain in each individual. To date, the current treatments for pancreatic pain involve administering 4 to 7 capsules per meal, 4 times a day; the capsules typically comprise a porcine-based pancreatic enzyme extract containing a mixture lipase, protease and amylase, e.g., Viokase®-16. In a Viokase® 16 enzyme capsule regimen, for example, about 2 to 3.5 grams of total pancreatic enzymes would be administered during each meal.

Exogenous pancreatic proteases should be administered free of enteric coating in order to have the desired activity in the duodenum (V. Singh et al., Gastroenterology Reports 5, 110-116, (2003)). However, absent an enteric coating, exogenous pancreatic proteases are typically administered with an acid-suppressing agent, such as a proton pump inhibitor or an $H_2$ receptor antagonist, in order to ensure that the protease arrives in duodenum with the desired activity (Ibid, 113). Proton pump inhibitors used for this purpose include, e.g., Omeprazole (Losec), Esomeprazole (Nexium), Lansoprazole (Zoton), Pantoprazole (Protium), Rabeprazole sodium (Pariet) and $H_2$ receptor antagonists include, e.g., Cimetidine (Tagamet, Dyspamet), Famotidine (Pepcid), Nizatidine (Axid), Ranitidine (Zantac), Ranitidine bismuth citrate (Pylorid).

One of the advantages of the methods of this invention is that the non-pancreatic protease may be administered as a solid form to a mammal without the need for enteric coatings or for the addition of acid-suppressing agents. Because microbially-derived proteases, such as fungal proteases, are more stable toward stomach acid than pancreatic enzymes, the need for acid-suppressing agents is minimal or non-existent.

Conventional proteases used to control maldigestion are typically administered in capsule form, because it is generally believed that proteins are not stable during tablet compression. The present invention provides non-pancreatic proteases in the form of a compressed tablet that remain active without an enteric coating and without an acid-suppressing agent.

In order to test the feasibility and activity of compressed tablets of protease for treatment of methods according to this invention, the following tests were performed. Three formulations shown in Table 9 were prepared by removing seaprose (Aspergillus melleus, crystalline SAP) from cold storage and allowing it to warm to room temperature for less than 2 hours. A placebo blend was prepared by combining all excipients for a given formulation into a polyethylene bag and dry blending. For example, a 200 mg tablet was prepared by measuring and mixing 140 mg of placebo blend and 60 mg of seaprose (81,600 USP units), transferring this blend to a die cavity of a single punch apparatus and applying compression to the blend to form a tablet. Seaprose without excipients (pure form) was prepared by weighing 100 mg of seaprose, transferring it to a die cavity of a single punch apparatus and compressing it into a tablet form. We found that a 60 mg quantity of seaprose was too small of a quantity to be compressed by the compression tool used (Single Punch Tablet Compression Machine, Model MTCM-I, Globepharma, Inc.).

TABLE 9

Preparation of seaprose tablets

| Component | Tablet A wt/unit or mg/tablet | Tablet B wt/unit or mg/tablet | Tablet C wt/unit or mg/tablet |
|---|---|---|---|
| Seaprose (SAP) | 60.00 | 60.00 | 100.00 |
| Microcrys. Cellulose 103 | 114.00 | — | — |
| Anhydrous Emcompress | 114.00 | 114.00 | — |
| Crospovidone XL | 20.00 | 20.00 | — |
| Col. Silicon Dioxide | 3.00 | 3.00 | — |
| Talc | 2.00 | 2.00 | — |
| Mag. Stearate NO-BOV | 1.00 | 1.00 | — |
| Total | 200.00 | 200.00 | 100.00 |

TABLE 9-continued

Preparation of seaprose tablets

| Component | Tablet A wt/unit or mg/tablet | Tablet B wt/unit or mg/tablet | Tablet C wt/unit or mg/tablet |
|---|---|---|---|
| Compression force (PSI) | 1000 | 1000 | 1000 |
| Tablet Hardness (KP) | 17.3 | 7.1 | 8.3 |

TABLE 10

Summary of the activities of compressed tablets

| | Tablet A | Tablet B | Tablet C |
|---|---|---|---|
| | | Activity (%)* | |
| Powder (before compression) | 103.6 ± 2.0 | 110.5 ± 3.9 | 110.2 ± 4.6 |
| Tablet (after compression) | 83.3 ± 1.5 | 90.3 ± 2.8 | 85.8 ± 1.4 |

*The protease activities were measured using the USP protease assay referred to herein. The initial protease activity was 1439 USP units/mg. The composition of tablets A, B and C are described under Table 9.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the disclosure herein, including the appended claims.

We claim:

1. A method for treating abdominal pain in a mammal due to pancreatitis, the method comprising administering seaprose to said mammal.

2. A method for treating abdominal pain in a mammal due to pancreatitis, the method comprising the step of administering seaprose to said mammal, wherein the plasma cholecystokinin (CCK) level in said mammal after administering said seaprose is less than or at the same level as a plasma cholecystokinin (CCK) level in said mammal before administering said seaprose and remains less than or at the same level as the plasma cholecystokinin (CCK) level in said mammal before administering said seaprose for a period of time selected from the group consisting of:

(a) between zero and about 4 hours after administering said seaprose;

(b) between zero and about 8 hours after administering said seaprose; and (c) between zero and about 12 hours after administering said seaprose.

3. A method for treating abdominal pain in a mammal due to pancreatitis, the method comprising the step of administering seaprose to said mammal, wherein said seaprose causes a reduction in maximum plasma concentration (Cmax) of cholecystokinin (CCK) in said mammal as measured by comparing (a) said Cmax in the absence of said seaprose after food administration to (b) said Cmax in the presence of said seaprose after food administration, and wherein said reduction is selected from the group consisting of:

(i) at least about 10% to about 25% reduction;

(ii) at least about 25% to about 50% reduction;

(iii) at least about 50% to about 75% reduction; and (iv) at least about 75% to about 100% reduction.

4. A method for treating abdominal pain in a mammal due to pancreatitis, the method comprising the step of administering seaprose to said mammal, wherein said seaprose reduces the plasma cholecystokinin (CCK) level in said mammal as compared to the plasma cholecystokinin (CCK) level in said mammal before administering said seaprose.

5. A method for treating abdominal pain in a mammal due to pancreatitis, the method comprising administering seaprose to said mammal with food, wherein said seaprose reduces the maximum plasma concentration (Cmax) of CCK in said mammal as compared to the Cmax of CCK in said mammal without said seaprose being present during administration of food.

6. The method according to any one of claims 1 and 2-5, wherein said seaprose is in crystalline, semi-crystalline or amorphous form.

7. The method according to any one of claims 1 and 2-5, wherein said mammal is a human.

8. The method according to any one of claims 1 and 2-5, wherein said seaprose is administered in an amount from about 5,000 to about 1,000,000 USP units of protease activity per dose.

9. The method according to claim 8, wherein said seaprose is administered in an amount from about 5,000 to about 750,000 USP units of protease activity per dose.

10. The method according to claim 9, wherein said seaprose is administered in an amount from about 5,000 to about 500,000 USP units of protease activity per dose.

11. The method according to claim 10, wherein said seaprose is administered in an amount from about 5,000 to about 250,000 USP units of protease activity per dose.

12. The method according to any one of claims 1 and 2-5, wherein said seaprose is crosslinked with a crosslinker selected from the group consisting of: multifunctional crosslinkers, homobifunctional crosslinkers, heterobifunctional crosslinkers, zero-order crosslinkers, dialdehyde crosslinkers, halo-triazine crosslinkers, halopyrimidine crosslinkers, anhydride crosslinkers, halide crosslinkers, N-methylol compounds, diisocyanate crosslinkers, diisothiocyanate crosslinkers and aziridine crosslinkers.

13. The method according to any one of claims 1 and 2-5, wherein said seaprose is administered to said mammal as a liquid, a solid, a suspension or a dispersion.

14. The method according to any one of claims 1 and 2-5, wherein said seaprose is administered to said mammal by oral route.

15. The method according to claim 14, wherein said seaprose is administered to said mammal by oral route without co-administration of an acid-suppressing agent.

16. The method according to any one of claims 1 and 2-5, wherein said seaprose is administered to said mammal as a slurry, tablet, caplet, capsule or dragee.

17. The method according to any one of claims 1 and 2-5, wherein said seaprose is administered to said mammal as a non-enterically coated tablet.

18. The method according to claim 16, wherein said seaprose is administered to the mammal at a dose of between one and six tablets per meal, wherein said tablet comprises an active seaprose level selected from the group consisting of:

(a) between about 20 mg to about 500 mg;

(b) between about 50 mg to about 500 mg; and (c) between about 50 mg to about 250 mg.

19. The method according to claim 16, wherein said seaprose is administered to the mammal as one or more tablets providing an active seaprose dose per meal selected from the group consisting of:

(a) between about 1 mg per kg mammal and 10 mg per kg mammal;

(b) between about 1 mg per kg mammal and 3 mg per kg mammal; and (c) between about 1 mg per kg mammal and 2 mg per kg mammal.

20. The method according to any one of claims 1 and 2-5, wherein said seaprose is in the form of crystals.

21. The method according to claim 1, wherein the seaprose is provided in a composition comprising seaprose.

22. The method according to claim 2, wherein the seaprose is provided in a composition comprising seaprose.

23. The method according to claim 2, wherein the plasma cholecystokinin (CCK) level in said mammal after administering said seaprose remains less than or at the same level as the plasma cholecystokinin (CCK) level in said mammal before administering said seaprose for a period of between zero and about 4 hours after administering said seaprose.

24. The method according to claim 2, wherein the plasma cholecystokinin (CCK) level in said mammal after administering said seaprose remains less than or at the same level as the plasma cholecystokinin (CCK) level in said mammal before administering said seaprose for a period of between zero and about 8 hours after administering said seaprose.

25. The method according to claim 2, wherein the plasma cholecystokinin (CCK) level in said mammal after administering said seaprose remains less than or at the same level as the plasma cholecystokinin (CCK) level in said mammal before administering said seaprose for a period of between zero and about 12 hours after administering said seaprose.

26. The method according to claim 3, wherein the seaprose is provided in a composition comprising seaprose.

27. The method according to claim 3, wherein said reduction is at least about 10% to about 25% reduction.

28. The method according to claim 3, wherein said reduction is at least about 25% to about 50% reduction.

29. The method according to claim 3, wherein said reduction is at least about 50% to about 75% reduction.

30. The method according to claim 3, wherein said reduction is at least about 75% to about 100% reduction.

31. The method according to claim 4, wherein the seaprose is provided in a composition comprising seaprose.

32. The method according to claim 5, wherein the seaprose is provided in a composition comprising seaprose.

33. The method according to claim 21, wherein said seaprose is in crystalline, semi-crystalline or amorphous form.

34. The method according to claim 22, wherein said seaprose is in crystalline, semi-crystalline or amorphous form.

35. The method according to claim 26, wherein said seaprose is in crystalline, semi-crystalline or amorphous form.

36. The method according to claim 31, wherein said seaprose is in crystalline, semi-crystalline or amorphous form.

37. The method according to claim 32, wherein said seaprose is in crystalline, semi-crystalline or amorphous form.

38. The method according to claim 21, wherein said composition further comprises an excipient or carrier.

39. The method according to claim 38, wherein said excipient is selected from the group consisting of: salts, alcohols, carbohydrates, proteins, lipids, surfactants, polymers and polyamino acids.

40. The method according to claim 22, wherein said composition further comprises an excipient or carrier.

41. The method according to claim 40, wherein said excipient is selected from the group consisting of: salts, alcohols, carbohydrates, proteins, lipids, surfactants, polymers and polyamino acids.

42. The method according to claim 26, wherein said composition further comprises an excipient or carrier.

43. The method according to claim 42, wherein said excipient is selected from the group consisting of: salts, alcohols, carbohydrates, proteins, lipids, surfactants, polymers and polyamino acids.

44. The method according to claim 31, wherein said composition further comprises an excipient or carrier.

45. The method according to claim 44, wherein said excipient is selected from the group consisting of: salts, alcohols, carbohydrates, proteins, lipids, surfactants, polymers and polyamino acids.

46. The method according to claim 32, wherein said composition further comprises an excipient or carrier.

47. The method according to claim 46, wherein said excipient is selected from the group consisting of: salts, alcohols, carbohydrates, proteins, lipids, surfactants, polymers and polyamino acids.

48. The method according to claim 21, wherein said composition further comprises one or more enzymes selected from the group consisting of: lipase and amylase.

49. The method according to claim 22, wherein said composition further comprises one or more enzymes selected from the group consisting of: lipase and amylase.

50. The method according to claim 26, wherein said composition further comprises one or more enzymes selected from the group consisting of: lipase and amylase.

51. The method according to claim 31, wherein said composition further comprises one or more enzymes selected from the group consisting of: lipase and amylase.

52. The method according to claim 32, wherein said composition further comprises one or more enzymes selected from the group consisting of: lipase and amylase.

53. The method according to claim 18, wherein said tablet comprises an active seaprose level between about 20 mg to about 500 mg.

54. The method according to claim 18, wherein said tablet comprises an active seaprose level between about 50 mg to about 500 mg.

55. The method according to claim 18, wherein said tablet comprises an active seaprose level between about 50 mg to about 250 mg.

56. The method according to claim 19, wherein said active seaprose is administered to the mammal as one or more tablets providing an active seaprose dose per meal of between about 1 mg per kg mammal and 10 mg per kg mammal.

57. The method according to claim 19, wherein said active seaprose is administered to the mammal as one or more tablets providing an active seaprose dose per meal of between about 1 mg per kg mammal and 3 mg per kg mammal.

58. The method according to claim 19, wherein said active seaprose is administered to the mammal as one or more tablets providing an active seaprose dose per meal of between about 1 mg per kg mammal and 2 mg per kg mammal.

* * * * *